(12) United States Patent
Santhanam et al.

(10) Patent No.: US 10,205,046 B2
(45) Date of Patent: *Feb. 12, 2019

(54) THERMO-ELECTRICALLY PUMPED LIGHT-EMITTING DIODES

(71) Applicant: Massachusetts Institute of Technology, Cambridge, MA (US)

(72) Inventors: Parthiban Santhanam, Cambridge, MA (US); Dodd Joseph Gray, San Francisco, CA (US); Rajeev Jagga Ram, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/632,550

(22) Filed: Jun. 26, 2017

(65) Prior Publication Data

US 2017/0294551 A1    Oct. 12, 2017

Related U.S. Application Data

(63) Continuation of application No. 14/459,681, filed on Aug. 14, 2014, now Pat. No. 9,722,144.

(Continued)

(51) Int. Cl.
*H01L 33/00* (2010.01)
*H01L 23/34* (2006.01)
(Continued)

(52) U.S. Cl.
CPC ......... *H01L 33/0004* (2013.01); *G01J 3/108* (2013.01); *G01J 3/42* (2013.01);
(Continued)

(58) Field of Classification Search
None
See application file for complete search history.

(56) References Cited

U.S. PATENT DOCUMENTS

| 2,898,743 A | 8/1959 | Bradley |
| 4,628,695 A | 12/1986 | Berdahl |

(Continued)

FOREIGN PATENT DOCUMENTS

| DE | 202007010981 U1 | 11/2007 |
| JP | 2012-119409 A | 6/2012 |

(Continued)

OTHER PUBLICATIONS

Dousmanis et al. "Evidence of Refridgerating action by means of photon emission" in Physical Review vol. 133, p. A316. Published by American Physical Society in 1964.*

(Continued)

*Primary Examiner* — Jesse Y Miyoshi
*Assistant Examiner* — Tuan A Hoang
(74) *Attorney, Agent, or Firm* — Smith Baluch LLP

(57) ABSTRACT

Contrary to conventional wisdom, which holds that light-emitting diodes (LEDs) should be cooled to increase efficiency, the LEDs disclosed herein are heated to increase efficiency. Heating an LED operating at low forward bias voltage (e.g., $V<k_BT/q$) can be accomplished by injecting phonons generated by non-radiative recombination back into the LED's semiconductor lattice. This raises the temperature of the LED's active rejection, resulting in thermally assisted injection of holes and carriers into the LED's active region. This phonon recycling or thermo-electric pumping process can be promoted by heating the LED with an external source (e.g., exhaust gases or waste heat from other electrical components). It can also be achieved via internal heat generation, e.g., by thermally insulating the LED's diode structure to prevent (rather than promote) heat dissipation. In other words, trapping heat generated by the LED within the LED increases LED efficiency under certain bias conditions.

18 Claims, 20 Drawing Sheets

Related U.S. Application Data

(60) Provisional application No. 61/866,892, filed on Aug. 16, 2013.

(51) Int. Cl.
```
H01L 33/64      (2010.01)
G01N 21/3577    (2014.01)
G01J 3/10       (2006.01)
G01J 3/42       (2006.01)
G01J 3/44       (2006.01)
H01L 33/30      (2010.01)
H01L 33/48      (2010.01)
H01L 33/20      (2010.01)
H01L 33/36      (2010.01)
H01L 33/44      (2010.01)
H01L 25/075     (2006.01)
H01L 33/02      (2010.01)
```

(52) U.S. Cl.
CPC ........ *G01J 3/4412* (2013.01); *G01N 21/3577* (2013.01); *H01L 23/345* (2013.01); *H01L 33/20* (2013.01); *H01L 33/30* (2013.01); *H01L 33/36* (2013.01); *H01L 33/44* (2013.01); *H01L 33/48* (2013.01); *H01L 33/645* (2013.01); *G01N 2201/062* (2013.01); *H01L 25/0753* (2013.01); *H01L 33/02* (2013.01); *H01L 2924/0002* (2013.01)

(56) References Cited

U.S. PATENT DOCUMENTS

| | | | |
|---|---|---|---|
| 5,200,966 A | | 4/1993 | Esterowitz et al. |
| 5,563,422 A | | 10/1996 | Nakamura et al. |
| 6,948,829 B2 | * | 9/2005 | Verdes ............ F21V 3/00 315/71 |
| 8,333,860 B1 | | 12/2012 | Bibl et al. |
| 8,349,116 B1 | | 1/2013 | Bibl et al. |
| 8,383,506 B1 | | 2/2013 | Golda et al. |
| 8,415,767 B1 | | 4/2013 | Golda et al. |
| 8,415,768 B1 | | 4/2013 | Golda et al. |
| 8,415,771 B1 | | 4/2013 | Golda et al. |
| 8,426,227 B1 | | 4/2013 | Bibl et al. |
| 8,518,204 B2 | | 8/2013 | Hu et al. |
| 8,552,436 B2 | | 10/2013 | Bibl et al. |
| 8,558,243 B2 | | 10/2013 | Bibl et al. |
| 8,569,115 B1 | | 10/2013 | Golda et al. |
| 8,573,469 B2 | | 11/2013 | Hu et al. |
| 8,646,505 B2 | | 2/2014 | Bibl et al. |
| 9,557,215 B2 | | 1/2017 | Santhanam et al. |
| 9,722,144 B2 | | 8/2017 | Santhanam et al. |
| 2004/0104395 A1 | | 6/2004 | Hagimoto et al. |
| 2004/0245912 A1 | | 12/2004 | Thurk et al. |
| 2006/0091788 A1 | | 5/2006 | Yan |
| 2008/0035953 A1 | * | 2/2008 | Beom ............ H01L 33/02 257/103 |
| 2008/0220535 A1 | | 9/2008 | Leboeuf et al. |
| 2009/0295265 A1 | | 12/2009 | Tabuchi et al. |
| 2010/0140635 A1 | * | 6/2010 | Ibbetson ............ H01L 33/46 257/98 |
| 2011/0107770 A1 | | 5/2011 | Oksanen et al. |
| 2011/0279054 A1 | * | 11/2011 | Katona ............ H01L 33/32 315/291 |
| 2013/0069077 A1 | * | 3/2013 | Song ............ H01L 51/5278 257/76 |
| 2013/0082236 A1 | | 4/2013 | Ramer et al. |
| 2013/0126098 A1 | | 5/2013 | Bibl et al. |
| 2013/0126827 A1 | | 5/2013 | Bibl et al. |
| 2013/0128585 A1 | | 5/2013 | Bibl et al. |
| 2013/0200414 A1 | | 8/2013 | Hsu et al. |
| 2013/0210194 A1 | | 8/2013 | Bibl et al. |
| 2013/0230069 A1 | | 9/2013 | Cheng et al. |
| 2014/0008813 A1 | | 1/2014 | Golda et al. |
| 2014/0048909 A1 | | 2/2014 | Golda et al. |
| 2014/0061687 A1 | | 3/2014 | Hu et al. |
| 2014/0084482 A1 | | 3/2014 | Hu et al. |
| 2014/0362586 A1 | | 12/2014 | Wu |
| 2014/0369036 A1 | | 12/2014 | Feng |

FOREIGN PATENT DOCUMENTS

| | | |
|---|---|---|
| KR | 10-2013-0038061 A | 4/2013 |
| WO | WO 2010/106232 A2 | 9/2010 |

OTHER PUBLICATIONS

Narukawa et al. "White light emitting diodes with super-high luminous efficacy" in Journal of Physics D: Applied Physics, vol. 43, p. 354002. Published by IOP Publishing in 2010.*

Krames et al. "High power truncated-inverted-pyramid AlGaInP— GaP light emitting diode exhibiting 50 percent external quantum efficiency" in Applied Physics Letters vol. 75, p. 2365. Published by American Institute of Physics in 1999.*

Dousmanis et al. "Evidence of Refridgerating action by means of photon emission" in Physical Review vol. 133, p. A316. Published by American Physical Society in 1964. (Year: 1964).*

Narukawa et al. "White light emitting diodes with super-high luminous efficacy" in Journal of Physics D: Applied Physics, vol. 43, p. 354002. Published by IOP Publishing in 2010. (Year: 2010).*

Krames et al. "High power truncated-inverted-pyramid AlGaInP— GaP light emitting diode exhibiting 50 percent external quantum efficiency" in Applied Physics Letters vol. 75, p. 2365. Published by American Institute of Physics in 1999. (Year: 1999).*

Ban, D. et al., "Optimized GaAs/AlGaAs light-emitting diodes and high efficiency water-fused optical up-conversion devices", J. Appl. Phys., vol. 96, pp. 5243 (2004).

Berdahl, "Radiant refrigeration by semiconductor diodes," Journal of Applied Physics, vol. 58, p. 1369. Published by American Institute of Physics (1985).

Brodrick, J. "The Race is on for DOE's L Prize," NEMA Electroindustry, pp. 14-16 (Feb. 2009).

Cich, M. J. et al., "Bulk GaN based violet light-emitting diodes with high efficiency at very high current density," Applied Physics Letters 101, 223509 (2012).

Corrected Notice of Allowability dated Apr. 19, 2017 from U.S. Appl. No. 14/459,681, 10 pages.

Data Sheet for Ioffe LED, Ltd. Model LED21Sr, 1 page (Oct. 14, 2011).

Dousmanis et al., "Evidence of refrigerating action by means of photon emission in semiconductor diodes," Physical Review, vol. 133, pp. A316-A319. Published by American Physical Society (1964).

Extended European Search Report issued by the European Patent Office in regards to European Application No. 14836407.8, dated Dec. 23, 2016, 10 pages.

Final Office Action dated Jun. 3, 2016 from U.S. Appl. No. 13/969,225, 17 pages.

Final Office Action dated Dec. 4, 2015 from U.S. Appl. No. 14/459,681, 24 pages.

Gessman et al., "High efficiency AlGaInP light-emitting diodes for solid-state lighting applications," Journal of Applied Physics, vol. 95, p. 2203. Published by American Institute of Physics (2004).

Gray et al., "Design for enhanced thermo-electric pumping in light emitting diodes," Applied Physics Letter, vol. 103, 6 pages (Sep. 17, 2013).

Gray, D., "Thermal pumping of light-emitting diodes," Master thesis. Published by Massachusetts Institute of Technology, pp. 1-35, (2011).

Hall, R. N., "Electron-Hole Recombination in Germanium", Phys. Rev., vol. 87, p. 387 (1952).

Han, P. et al., "Numerical designing of semiconductor structure for optothermionic refrigeration," Journal of Applied Physics, 101(014506):1-4 (Jan. 2007).

(56) References Cited

OTHER PUBLICATIONS

Harder, N. P., "A hot-electron thermophotonic solar cell demonstrated by thermal up-conversion of sub-bandgap photons", Semicond. Sci. Technol., vol. 18, S270-S278 (2003).
Haynes, J. R. et al., "Radiation Resulting from Recombination of Holes and Electrons in Silicon", Phys. Rev., vol. 101, Issue 6, pp. 1676-1678 (1656).
Heikkilä, O. et al., "Ultimate limit and temperature dependency of light-emitting diode efficiency," J. Appl. Phys. 105, 093119; doi: 10.1063/1.3125514 (2009).
Heikkila, O. et al., "The challenge of unity wall plug efficiency: the effects of internal heating on the efficiency of light emitting diodes," Journal of Applied Physics, 107(033105):1-6 (Feb. 2010).
Hurni, C. A. et al., "Bulk GaN flip-chip violet light-emitting diodes with optimized efficiency for high-power operation," Applied Physics Letters 106, 031101; doi:10.1063/1.4905873 (2015).
Krames et al., High power truncated-inverted-pyramid AlGaInP/GaP light-emitting diodes exhibiting >50% external quantum efficiency, Applied Physics Letters, vol. 75, p. 2365. Published by American Institute of Physics (1999).
Krier at al., "Design considerations for uncooled InAs mid-infrared light emitting diodes grown by liquid phase epitaxy," Journal of Physics D: Applied Physics, vol. 39, No. 2, pp. 255-261 (Jan. 6, 2006).
Landsberg, P. T. et al. "Thermodynamic limits for some light-producing devices", Physical Review, vol. 166, No. 2, pp. 242-246 (Feb. 1968).
Landsberg, P. T. et al., "Thermodynamic energy conversion efficiencies", Journal of Applied Physics, vol. 51, No. 7, R1-R20 (Apr. 1980).
Lee, H. K. et al., "Thermal analysis and characterization of the effect of substrate thinning on the performances of GaN-based light emitting diodes", Phys. Status Solidi A, vol. 207, No. 6, pp. 1497-1504 (2010).
Lehovec, K. et al., "Light emission produced by current injected into a green silicon-carbide crystal", Physical Review, vol. 89, No. 1, pp. 20-25 (Jan. 1953).
Malshukov, A. G. et al., "Opto-thermionic refrigeration in semiconductor heterostructures," Physical Review Letters, 86:5570-5573 (Jun. 2001).
Malyutenko, V. et al., "High Temperature (T>300 K) light emitting diodes for 8-12μm spectral range", Infrared Phys. Technol., vol. 41, Issue 6, pp. 373-378 (2000).
Matveev et al., Journal of Modern Optics, vol. 49, pp. 743-756 (2002).
Mungan, C. E., "Radiation thermodynamics with applications to lasing and fluorescent cooling", American Journal of Physics, vol. 73, No. 4, pp. 315-322 (2005).
Narukawa, Y. et al., "White light emitting diodes with super-high luminous efficacy," J. Phys. D: Appl. Phys., 43, 354002 (2010).
Narukawa, Y., "Optical Refrigeration in light-emitting diodes", Electron Technol., vol. 13, pp. 61-72 (1982).
Nathan, M. I. et al., "High-energy emission in gas electroluminescent diodes", Physical Review, vol. 146, No. 2, pp. 570-574 (Jun. 1966).
Newman, R., "Optical studies of injected carriers. II. Recombination radiation in germanium", Phys. Rev., vol. 91, No. 6, pp. 1313-1314 (1653).
Nolas, G. S. et al., "Thermo-electrics: Basic Principles and New Materials Developments", Thermionic Refrigeration, Chapter 9, Springer-Verlag Berlin Heidelberg, 15 pages (2001).
Non-Final Office Action dated Jul. 30, 2015 from U.S. Appl. No. 14/459,681, 22 pages.
Non-Final Office Action dated Nov. 4, 2015 from U.S. Appl. No. 13/969,225, 21 pages.
Non-Final Office Action dated Dec. 2, 2016 from U.S. Appl. No. 14/459,681, 33 pages.
Notice of Allowance dated Mar. 24, 2017 from U.S. Appl. No. 14/459,681, 13 pages.
Notice of Allowance dated Sep. 26, 2016 from U.S. Appl. No. 13/969,225, 14 pages.
Notification of Transmittal of the International Search Report and the Written Opinion of the International Searching Authority in related PCT Application No. PCT/US2014/051012 dated Nov. 24, 2014, 9 pages.
Oksanen, J. et al., "Effects of photon transport, emission saturation and reflection losses on thermophotonic cooling", Presented at SPIE Photonics West Conference, San Francisco, USA, vol. 7951, pp. 79510H-1-79510H-7 (Jan. 2011).
Olsson, A., "Fabrication and Characterization of Thermophotonic Devices", Thesis presented for Master of Science in Technology, Aalto University, Department of Biomedical Engineering and Computational Science,) 55 pages (May 19, 2011).
Pipe, K. P. et al., "Bias-dependent peltier coefficient and internal cooling in bipolar devices", Physical Review B, vol. 66, pp. 125316-1-125316-11 (Sep. 2002).
Pipe, K. P. et al., "Comprehensive heat exchange model for a semiconductor laser diode", IEEE Photonics Technology Letters, vol. 15, No. 4, pp. 504-506 (Apr. 2003).
Pipe, K. P. et al., "Internal cooling in a semiconductor laser diode", IEEE Photonics Technology Letters, vol. 14, No. 4, pp. 453-455 (Apr. 2002).
Santhanam, P. et al., "Electro-Luminescent Cooling: Light Emitting Diodes Above Unity Efficiency," Laser Refrigeration of Solids VI, edited by Richard I. Epstein, Denis V. Seletskiy, Mansoor Sheik-Bahae, Proc. of SPIE vol. 8638, 863807 (2013).
Santhanam, P. et al., "Thermo-Photonics: Exploiting the Entropy of Photons in Energy Conversion," presentation at the University of California at Santa Barbara, Jan. 24, 2013.
Santhanam, P. et al., "Light-emitting diodes operating above unity efficiency for infrared absorption spectroscopy", Proc. of the 2012 International Photonics Conference, pp. 441-442 (Sep. 2012).
Santhanam, P. et al., "Thermoelectrically pumped light-emitting diodes operating above unity efficiency." Phys. Rev. Lett., vol. 108, 097403 (Feb. 2012).
Santhanam, P., "Generalized drift-diffusion for microscopic thermoelectricity", Master's of Science, Massachusetts Institute of Technology, Department of Electrical Engineering and Computer Science, 193 pages. (Aug. 7, 2009).
Schubert, E.F., "Light-Emitting Diodes," Cambridge University Press, 2nd Ed., pp. 195-196 (Jun. 19, 2006).
Shockley, W. et al., "Statistics of the recombinations of holes and electrons", Phys. Rev. vol. 87, No. 5, pp. 835-842 (1952).
Sotnikova et al., IEEE Sensors, "Low Voltage $CO_2$-Gas Sensor Based on III-V Mid-IR Immersion Lens Diode Optopairs: Where we are and and How Far we Can Go?," vol. 10, No. 2, pp. 225-234 (Feb. 2010).
Steele, R. V., "The Story of a New Light Source," Nat. Phot. 1, pp. 25-26 (2007).
Tauc, J., "The Share of Thermal Energy Taken from the Surroundings in the Electro-Luminescent Energy from a p-n Junction," Czechosl. Journ. Phys. 7:275-276 (1957).
The Next Generation of LED Filament Bulbs, LEDInside, http://www.ledinside.com/knowledge/2015/2/the next generation of led filament bulbs 11:18, judy.lin, 7 pages (Feb. 5, 2015).
Wang, J. B. et al., "Electroluminescence Cooling in Semiconductors", Conference on Lasers and Electro-Optics/Quantum Electronics and Laser Science (CLEO/QELS) Conference, 3 pages. (2005).
Weinstein, M. A., Thermodynamic limitation on the conversion of heat into light, Journal of the Optical Society of America, Published by the Optical Society of America in 1960, vol. 50, No. 6, 6 pages.
Xue, J. et al., "Thermally enhanced blue light-emitting diode," Applied Physics Letters 107, 121109 (2015); doi: 10.1063/1.4931365.
Yen, S.-T. et al., "Analysis of heterostructures for electroluminescent refrigeration and light emitting without heat generation," Journal of Applied Physics, 107(054513):1-4 (Mar. 2010).
Yu, S. Q. et al., "Fundamental mechanisms of electroluminescence refrigeration in heterostructure light emitting diodes", Proc. of SPIE, 6486(648604):1-6 (Jan. 2007).

* cited by examiner

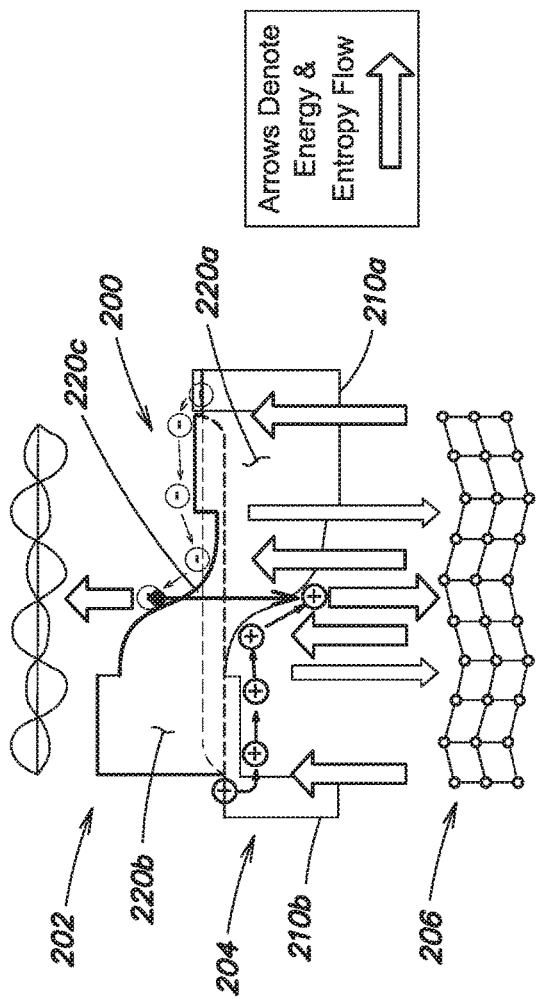
FIG. 2
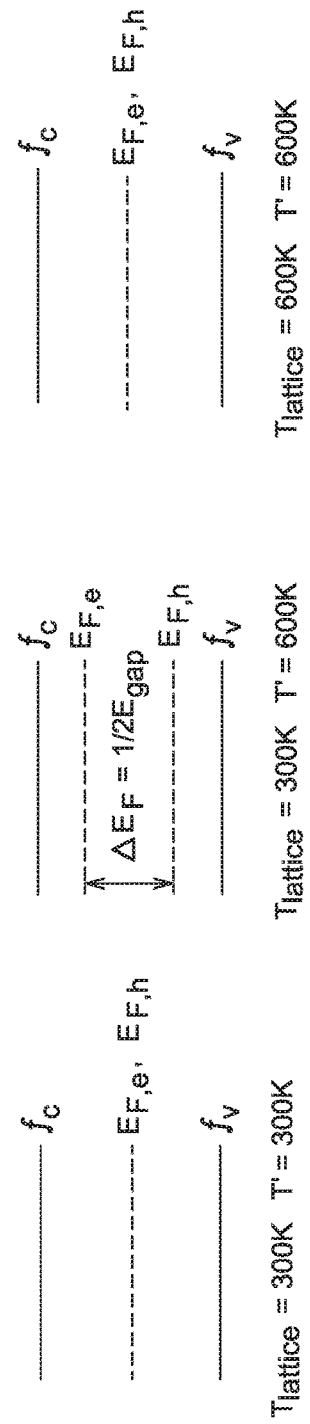
FIG. 3A  FIG. 3B  FIG. 3C

THERMO-ELECTRICALLY PUMPED LIGHT-EMITTING DIODES

CROSS-REFERENCE TO RELATED PATENT APPLICATIONS

This application is a continuation of U.S. application Ser. No. 14/459,681, now U.S. Pat. No. 9,722,144, entitled "Phonon-Recycling Light-Emitting Diodes" and filed on Aug. 14, 2016, which claims the priority benefit under 35 U.S.C. § 119(e) of U.S. Provisional Application No. 61/866,892, entitled "Thermo-Electrically Pumped Light-Emitting Diodes" and filed on Aug. 16, 2013. Each of these applications is incorporated herein by reference in its entirety.

This application is also related to U.S. application Ser. No. 13/969,225, now U.S. Pat. No. 9,557,215, entitled "Thermo-Electrically Pumped Light-Emitting Diodes" and filed on Aug. 16, 2013, which claims the priority benefit under 35 U.S.C. § 119(e) of U.S. Provisional Application No. 61/684,315, entitled "Photon-Recycling Light-Emitting Diode" and filed on Aug. 17, 2012. Each of these applications is incorporated herein by reference in its entirety.

BACKGROUND

In theory, a light-emitting diode (LED) may emit optical power higher than the driving electrical power, with the difference between the optical power and electrical power drawn from lattice heat. In other words, an LED's wall-plug efficiency $\eta$, which is the ratio of optical output power to electrical input power, that is greater than 100%. This phenomenon is known as electro-luminescent cooling, electro-luminescence refrigeration, opto-thermionic cooling, the operation of a "Thermischer Konverter," and thermo-photonic cooling.

In an electro-luminescently cooled LED, electrons and holes are first excited by small forward bias voltage V, which may be small enough that $qV<\hbar\omega$, where q is the charge of an electron and $\hbar\omega$ is the energy of the emitted photon. The total amount of electrical work supplied per excitation is the product of the electron's charge q and the bias voltage V; when qV is zero, the device is in thermodynamic equilibrium. Upon excitation, some of the electrons and holes relax by radiative recombination and generate photons that exit the LED. The fraction of electrons and holes that relax by radiative recombination is defined as the external quantum efficiency $\eta_{EQE}$. If each injected electron-hole pair emits a photon of energy $\hbar\omega$ with an external quantum efficiency $\eta_{EQE}$ but requires just qV in work for excitation, the wall-plug efficiency $\eta$ may be expressed as:

$$\eta = \frac{\hbar\omega}{qV} \cdot \eta_{EQE}$$

The observation of light emission with photon energy $\hbar\omega$ in excess of the electrical input energy per electron qV is readily accessible in LEDs at a variety of wavelengths. At these operating points, the electron population is pumped by a combination of electrical work and Peltier heat originating in the semiconductor's lattice; this thermo-electric heat exchange is non-uniformly distributed throughout the device. This phenomenon has been experimentally observed in a SiC emitter and connected physically to the Peltier effect. Nevertheless, net cooling, or equivalently electro-luminescence with wall-plug efficiency greater than unity, has eluded direct observation until recently.

Early measurements of light emission from semiconductor diodes were followed closely by theoretical developments. Beginning in 1957, a body of literature theoretically establishing the basic thermodynamic consistency of electro-luminescent cooling and exploring its limits began to emerge. In 1964, experimental results demonstrated that a GaAs diode could produce electro-luminescence with an average photon energy 3% greater than qV. Still, net cooling was not achieved due to competing non-radiative recombination processes, which led to a conclusion that a high value of $\eta_{EQE}$ was required for direct experimental observation of net electro-luminescent cooling.

More recently, several modeling and design efforts have aimed to raise the external quantum efficiency $\eta_{EQE}$ toward unity by maximizing the fraction of recombination that is radiative and employing photon recycling to improve photon extraction. More recent attempts to observe electro-luminescent cooling experimentally with a wall-plug efficiency $\eta$ near 100% have focused on the regime in which qV is equal to at least 50% of the material bandgap $E_g \approx \hbar\omega$. As qV is lowered well below $E_g$, the electron and hole populations decrease exponentially following a Boltzmann distribution with decreasing chemical potential. Since an excited electron in a direct bandgap semiconductor may relax either by recombining with a hole and emitting a photon, or alternatively by scattering into a state associated with a lattice imperfection and emitting phonons, small forward bias voltages $qV \ll E_g$ may be precluded by a requirement for high external quantum efficiency $\eta_{EQE}$.

SUMMARY

Embodiments of the present technology include light-emitting diodes (LEDs) and methods of operating LEDs. An exemplary LED comprises an active region to emit infrared or visible light via radiative recombination of electrons and holes and is configured to heat the active region so as to thermally assist injection of at least some of the electrons and the holes. In operation, the LED generates heat, at least some of which is confined within the LED to thermally assist injection of electrons and holes into an active region of the LED. For instance, the LED may be configured to generate the heat via its own inefficiency (waste heat). In operation, the heat generated by the LED may be confined and/or concentrated within the LED to promote the thermally assist injection of electrons and holes.

In some embodiments, the LED is configured to emit the light at low bias (e.g., at a bias voltage V such that $qV<\hbar\omega$). The active region may have a doping profile engineered to increase the LED's quantum efficiency at low bias. For instance, the active region may comprise a heterojunction or a homojunction. The LED may also include a micro-structure, in thermal communication with the active region, to increase heat transfer to and/or photon extraction from the active region.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 2 is a simplified band diagram depicting entropy and energy flux in a conventional LED.

FIG. 3A is a band diagram of a two-level system in equilibrium.

FIG. 3B is a band diagram of an electrically excited two-level system.

FIG. 3C is a band diagram of a thermally excited two-level system.

DETAILED DESCRIPTION

Figure 1A:
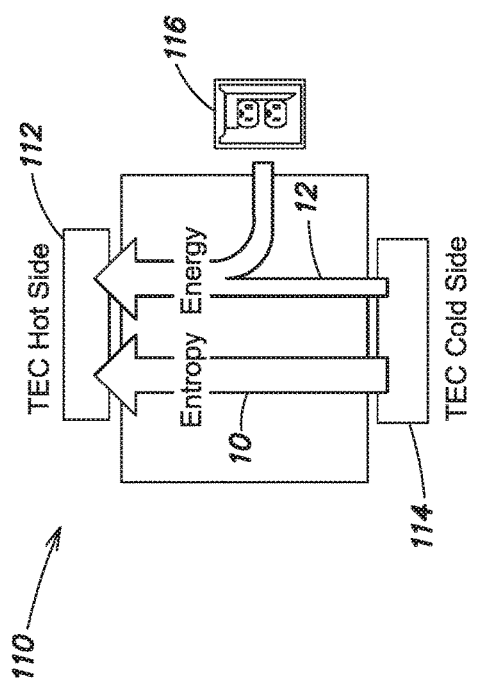
FIG. 1A depicts energy and entropy flows in a Carnot-efficient thermo-electric cooler (TEC).

Conventional light-emitting diodes (LEDs) are packaged with the goal of heat-sinking the diode as well as possible so that the junction temperature remains as low as possible. In doing so, the thermal energy generated internally by non-radiative recombination, carrier leakage, photon re-absorption, and other imperfections in the electrical-to-optical power conversion process is lost to the environment and does not contribute to optical output power. This is typically acceptable because these imperfections become stronger and further degrade performance with increasing temperature. In fact, many previous LEDs incorporate heat-spreading techniques that decrease the thermal resistance between the p-n junction (the active region) in the LED and the environment to keep the junction temperature from rising far above the ambient temperature.

Contrary to the conventional wisdom, which holds that LEDs should be cooled for maximum efficiency, increasing an LED's operating temperature (e.g., to about 400 K, 500 K, or 600 K) actually raises its efficiency under certain conditions (e.g., at low bias, when the overall wall-plug efficiency is below unity) as explained in greater detail below. Consequently, embodiments of the present disclosure include LEDs that are configured to operate with junctions at high temperatures so as to increase efficiency of generating incoherent electromagnetic radiation (light) from electricity. As explained in greater detail below, raising the LED's temperature allows thermal energy to assist the pumping process internal to the LED.

More specifically, concentrating heat within the LED permits the LED to recycle excess thermal energy from non-radiative recombination to pump the electrons and/or holes into the LED's active area, thereby increasing efficiency. In the high-temperature regime, the LED operates more efficiently with increasing temperature (e.g., at output powers between about 100 pW and about 10 And at very low power (e.g., less than 100 pW), an LED may operate so efficiently that the amount of excess heat available to be recycled is negative, corresponding to a cooling effect, in which case the LED could be used for solid-state refrigeration.

Depending on the embodiment, an inventive LED's operating temperature may be elevated using an external heat source and/or via phonon recycling, also known as thermo-electric pumping. In phonon recycling, non-radiative recombination processes and internal reabsorption of photons produce phonons that are absorbed by the semiconductor lattice forming the LED's active region. Put differently, the filament's electronic charge carriers may not be in equilibrium with the filament's lattice vibrations due to an applied voltage that creates a Fermi-level separation to drive light emission.

To exploit phonon recycling, an LED may be forward biased, e.g., at a bias voltage V chosen to satisfy the inequality $qV \leq \hbar\omega$, where q is the charge of an electron and $\hbar\omega$ is the energy of the emitted photon. For an LED that emits light at a wavelength of about 400 nm to about 700 nm, for example, the bias voltage may be less than about 1.7 V to about 3.1 V. For an LED that emits near-infrared light (e.g., about 1300 nm to about 1600 nm), the bias voltage may be less than about 0.77 V to about 0.95 V. And for an LED that emits mid-infrared light (e.g., about 2.0 μm to about 6.5 μm), the bias voltage may be less than about 0.19 V to about 0.62 V.

In addition, the LED should be heated to a temperature above the ambient temperature (i.e., above the temperature of the surrounding environment and of any surrounding electronic apparatus. In some cases, the LED may be the hottest thing in its immediate thermal environment.

To keep the LED hotter than its surroundings, the LED may be thermally isolated from other equipment, e.g., by increasing the thermal resistance between the LED's junction (active area) and the surrounding environment. This increased thermal resistance may be due to thermally isolating/insulating packaging that concentrates the heat generated within the LED. For example, an inventive LED may include an electro-thermal filament whose wavelength-selective emission is based on the filament's electronic structure. This filament may be surrounded by an inert gas or other insulating fluid to promote thermo-electrical pumping (phonon recycling). Alternatively, or in addition, an inventive LED's active region may also be thermally isolated using solid insulating material to improve the quality of the active region's thermal isolation and high-temperature material stability so as to cause the LED to heat itself while in operation.

Although phonon recycling may limit an inventive LED's efficiency to less than 100%, good thermal isolation may make losses required to maintain the elevated device temperature may be small compared to the output power. As a result, an inventive LED with good thermal isolation may operate with a wall-plug efficiency exceeding 50%. For instance, concentrating excess heat to raise an inventive LED's filament temperature to 320° C. could lead to production of about 130 μW/cm² of infrared optical power at 50% wall-plug efficiency, which is at least 100 times higher than the efficiency of conventional mid-IR sources. External heating (e.g., via exhaust or thermal dissipation from other sources) could raise the device's wall-plug efficiency above 100%.

Applications of Phonon-Recycling LEDs

The phonon-recycling LEDs disclosed herein can be used for a wide variety of applications, including those that benefit from low-brightness illumination or solid-state refrigeration. For instance, a phonon-recycling LED can be used to generate mid-infrared (mid-IR) light for spectroscopy applications, such as down-hole fluid analysis in oil and gas exploration and recovery. Other applications include generating visible light for ambient illumination, LED-based displays, optical communications, and illumination via fiber optic probes as laid out in greater detail below.

Mid-IR spectroscopy is particularly useful in the oil and gas sector, where spectroscopic systems are used to analyze fluid as it is produced from oil wells. For example, the Red Eye® sold by Weatherford International Ltd. uses near-infrared spectroscopic data to estimate the water-cut (i.e., the water-to-oil ratio of produced fluid) at the surface of an oil extraction site. Several other oilfield services companies also sell competing products that acquire similar spectroscopic data, both at the surface and in the high-temperature environments found downhole. In fact, embodiments of the proposed light source may be more robust to (and may benefit from) high-temperature environments.

Most commercially available spectroscopy-based analysis equipment for oil and gas exploration and production operates in the visible and near-infrared wavelength ranges, e.g., at wavelengths of less than about 2 μm. However, longer wavelength spectroscopy also provide extremely valuable information for characterizing new and existing oilfields. In particular, the detection of $H_2S$, which absorbs light strongly at wavelengths around 4.23 μm, could be used to determine when pressurizing fluid has leaked into the fluid being extracted during new artificial lift processes. Moreover, efficient sources in the mid-infrared could enable the next generation of analysis equipment to characterize the distribution of hydrocarbon lengths in real time as crude oil is produced, with a variety of benefits for the oil extraction industry.

Examples of the efficient light sources disclosed herein could also be used in other high-temperature and power-constrained environments. For example, a phonon-recycling LED could be used for online monitoring of combustion gases at high temperatures, e.g., in exhaust stacks, car and truck tail pipes, etc. An infrared, phonon-recycling LED could be used in a highly power-constrained free-space communication system, such as one used to send data from spacecraft to other satellites or back to Earth. Moreover, the blackbody radiation emitted at temperature could hide the signal emitted by the LED, enabling covert free-space communications. In addition, thermo-electrically pumped LEDs may be electrically excited to achieve photon emission on timescales faster than typical thermal time constants for solids of similar sizes. As a result, the arbitrarily efficient generation of photons at low bias may offer a new platform to test the limits of energy-efficient electromagnetic communication.

The LED as a Thermodynamic Machine

In statistical mechanics, the word "heat" is used to refer to any form of energy which possesses entropy. This usage applies equally to forms of energy referred to colloquially as "heat," such as the kinetic energy in the relative motion of the molecules in a gas or the constant vibrations of atoms in a crystal lattice, as well as those for which the entropy is frequently less relevant, such as the kinetic energy in the relative motion of electrons and holes in a semiconductor or the thermal vibrations of the electromagnetic field in free space. The Laws of Thermodynamics, which govern the flow of heat, are formulated independently of the laws which govern the deterministic trajectories of mechanical systems, be they classical or quantum. As a result concepts such as the Carnot limits for the efficiency of various energy conversion processes apply equally well to the gases and solid cylinder walls of an internal combustion engine as to the electrons, holes, and photons in a modern LED.

Figure 1B:
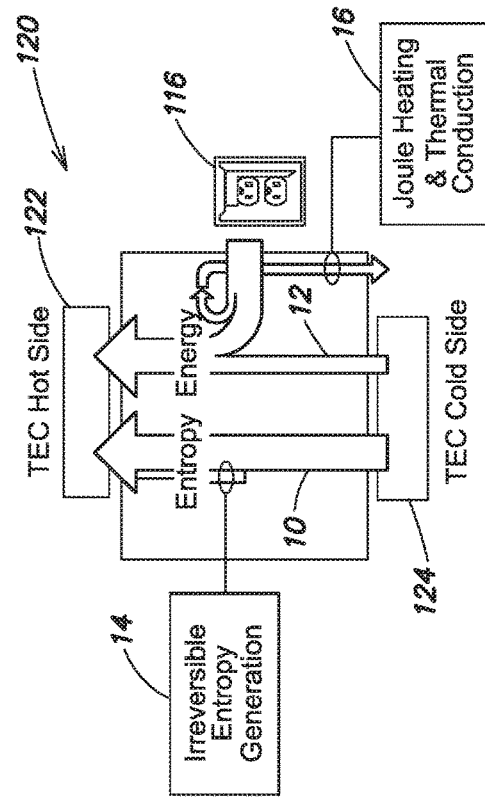
FIG. 1B depicts energy and entropy flows in a TEC with common sources of irreversibility.

FIGS. 1A-1D illustrate energy and entropy flows in idealized and real thermo-electric coolers (TECs) and LEDs. FIG. 1A shows that, for an idealized TEC 110, entropy 10 and energy 12 flow from the TEC's cold side 114 to its hot side 112. Energy 12 also flows from an external power supply (wall plug 116) to the TEC's hot side 112. In a real TEC 120, irreversibly generated entropy 14 flows to the hot side 122, and joule heating and thermal conduction 16 cause energy to flow to the cold side 124 as shown in FIG. 1B.

Figure 1C:
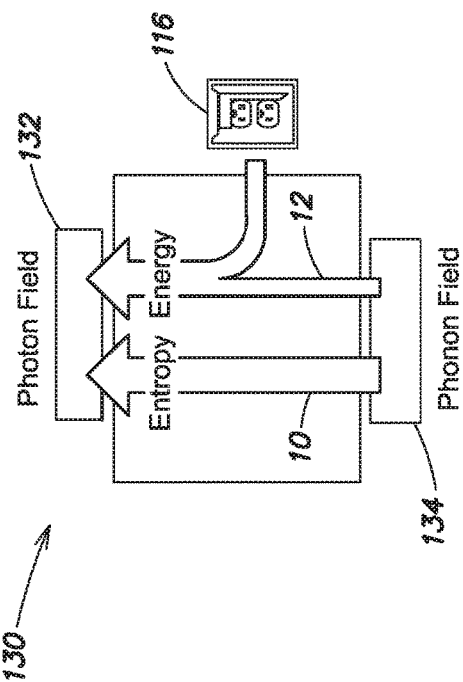
FIG. 1C depicts energy and entropy flows in a Carnot-efficient light-emitting diode (LED).
Figure 1D:
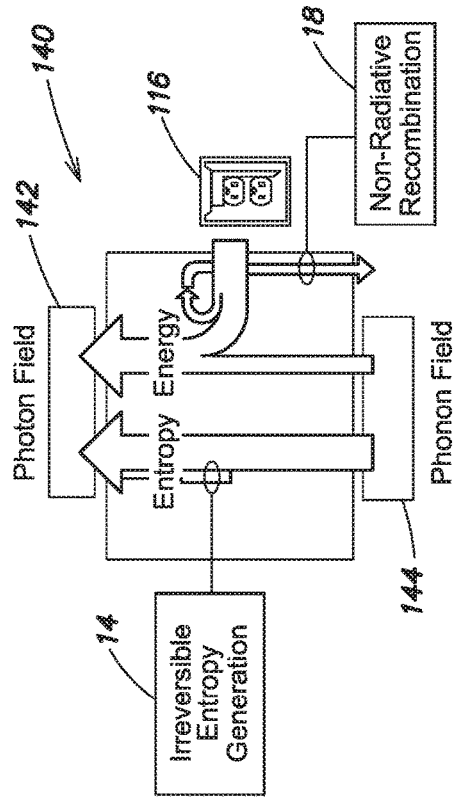
FIG. 1D depicts energy and entropy flows in an LED with common sources of irreversibility.

FIGS. 1C and 1D show flows of entropy 10 and energy 12 between a photon field 132 and a phonon field 134 in an idealized LED 130 and a real LED 140, respectively, organized in the canonical picture of a thermodynamic heat pump. In FIG. 1C, entropy 10 and energy 12 from the phonon field 134 to the photon field 132, with additional energy flowing from the wall plug 116 to the photon field 132. In FIG. 1D, irreversibly generated entropy 14 flows to the photon field 142, and non-radiative recombination 18 contributes to the phonon field 144.

FIGS. 1A-1D show that an LED can be considered to be an electronic device which takes entropy-free electrical work as input and emits incoherent light which carries entropy. Instead of irreversibly generating the entropy that it ejects into the photon reservoir, an LED may absorb it from another reservoir at finite temperature, such as the phonon bath. More specifically, an LED may absorb heat from the phonon bath and deposit it into the photon field in much the same way that a thermo-electric cooler (TEC) absorbs heat from its cold side and deposits the heat on its hot side.

In the reversible limit the flows of energy and entropy are highly analogous for an LED and a TEC. Moreover, in both the LED and TEC, the Peltier effect is responsible for the absorption of lattice heat by electrons and holes. Electrical work is being used to pump entropy from one reservoir to another instead of simply creating it through irreversible processes. Thus, an LED can be considered as a thermodynamic heat pump.

An amount of heat $T_{\delta S}$ comes with each bit of entropy $\delta S$ absorbed on net from the phonon reservoir at finite temperature. Since input and output power must balance in steady-state, the rate at which this heat and the input electrical work enter the system (both measured in Watts) should equal the rate at which heat is ejected into the photon reservoir (also measured in Watts). That is to say, when lattice heat is being absorbed on net an LED's wall-plug efficiency η (or equivalently its heating coefficient of performance), defined as the ratio of output optical power to input electrical power, exceeds unity.

Reservoir Temperatures

When an LED is operating above unity efficiency, heat may be extracted continuously from the lattice by the electronic system. Due to the large heat capacity of the lattice relative to the electron-hole system, the phonon field of the semiconductor diode may act very nearly as a perfect reservoir. That is to say, the other statistical subsystems that interact with the phonon field may deposit or withdraw any amount of energy ΔU from the phonon field so long as the change in energy is accompanied by a proportional amount of entropy ΔS. The constant of proportionality is given by the lattice temperature, yielding the following equation for a perfect phonon reservoir:

$$\Delta U = T_{lattice} \delta S \qquad (1)$$

In some situations, the lattice may remain slightly cooled compared to its surroundings, possibly due to the large but finite heat capacity of the phonon bath and its large but finite thermal conductance to ambient temperature surrounding. As a result, heat may be continuously conducted into the LED from the environment in steady-state. Put differently, the LED may experience self-cooling rather than self-heating.

In contrast, the heat capacity of the photon field in the relevant range of wavelengths may not be much larger than that of the electron-hole system. Furthermore, when the LED is emitting light, the optical field of the outgoing radiation modes may not be in equilibrium at ambient temperature. Nevertheless, the optical field emitted by the LED can be analyzed thermodynamically as follows.

Incoherent electromagnetic radiation that originates in an LED is capable of carrying entropy, just like electromagnetic radiation from a hot blackbody. Incoherent light may therefore be considered to be a type of heat in the statistical-mechanical sense mentioned above. The ratio of the rate at which radiation carries away energy to the rate at which it carries away entropy gives its flux temperature:

$$T_f = \frac{dU/dt}{dS/dt} \qquad (2)$$

Although this notion of temperature may be used to calculate the thermodynamic limits of power-conversion efficiency, the rate of entropy flux in light can be difficult to measure directly. Fortunately, there is a more intuitive definition of the temperature of light. Consider two bodies that are each perfectly thermally isolated from their environments (e.g., by adiabatic walls) and similarly isolated from each other. Suppose the first body has energy $U_1$ and entropy $S_1$ and likewise the second body has energy $U_2$ and entropy $S_2$. If the insulating boundary between the bodies is replaced with a boundary that permits the flow of energy, the total energy $U_1+U_2$ may flow to rearrange itself in the way which maximizes the total entropy. The flow may stop only when the addition of a differential amount of energy δU to either body results in the same fractional increase in the number of available micro-states for that body (i.e., the same increase in its entropy). Equivalently, the flow of energy stops when the bodies have equal temperature:

$$\frac{\partial S_1}{\partial U_1} \bigg/ \frac{1}{T_1} = \frac{1}{T_2} = \frac{\partial S_2}{\partial U_2} \qquad (3)$$

Now consider a similar scenario in which the first body is an LED and the second body is a perfect blackbody radiator. To begin, both bodies are adiabatically isolated from their environments and from each other. In the case of the blackbody radiator, the walls may be a surrounding surface made of mirrors, such that the blackbody radiator has zero emissivity. In the case of the LED, the adiabatic walls form a cavity with perfect reflectivity, such that each photon emitted by the LED reflects off a mirror and returns to the LED's active region to generate a quantum of reverse-current. Assume no non-radiative recombination occurs. The LED is on, but is in steady-state and consumes no power. Assume that the bodies have no means of exchanging energy other than through photons and that to begin the boundary between them is also a perfectly reflecting mirror.

If the wall separating the LED and the blackbody radiator is modified to transmit a small amount of light over a narrow range of wavelengths centered at $\lambda_0$, energy may flow on net from the body with higher spectral power density (I(λ) in W m$^{-2}$ nm$^{-1}$ str$^{-1}$) to the body with lower power spectral density at $\lambda_0$. If the LED is perfectly incoherent, the photons flowing in either direction may carry entropy, and therefore can be termed 'heat' in the statistical mechanical sense. Since heat may only flow from high temperature to low temperature, the equilibrium condition for the LED and the blackbody radiator may be satisfied when $I_1(\lambda_0)=I_2(\lambda_0)$. Since the relationship between intensity and temperature for a perfect blackbody is given by the Planck radiation law, the brightness temperature $T_B$ of an incoherent source can be defined as the temperature of a blackbody radiator whose spectral intensity equals that of the emitter at the wavelength and emission direction of interest:

$$I_{emitter}(\lambda_0) = I_{blackbody}(\lambda_0; T_B) = \frac{4\hbar\pi^2 c^2}{\lambda_0^5} \left\{ \exp\left[\frac{\hbar(2f\pi c/\lambda_0)}{k_B T_B}\right] - 1 \right\}^{-1} \qquad (4)$$

Unlike the color temperature of radiation commonly used in the lighting and display spaces, a longer-wavelength emitter is not necessarily cooler than a short-wavelength emitter. The linewidth, angular extent, wavelength, and intensity of the source may affect the source's temperature. For instance, variations in these factors may result in thermodynamically cold emission from a blue LED or thermodynamically hot emission from a red LED. That is to say, a source may have a relatively cool flux photon temperature $T_F$ and a cool brightness photon temperature $T_B$ even when emitting blue light. For more information on the distinction between the flux and brightness photon temperatures, see, e.g., M. A. Weinstein, "Thermodynamic limitation on the conversion of heat into light," J. Opt. Soc. Am. 50, 597-602 (1960).

Since the temperature of an incoherent photon flux is essentially a measure of its power spectral intensity, the Second Law of Thermodynamics places a different efficiency constraint on emitters of different spectral intensity. As a function of lattice temperature and emitter intensity, the Carnot limit may be expressed compactly as follows:

$$\eta \leq \eta_{Carnot} = \frac{T_{photon}(I)}{T_{photon}(I) - T_{lattice}} \quad (5)$$

For bright sources (e.g., $I(\lambda) \gg I_{blackbody}(\lambda; T_{lattice})$), the LED pumps heat against the large temperature difference between the lattice and the outgoing photon field. This results in a maximum efficiency, even for a perfect Carnot-efficient LED, which exceeds unity but only slightly. For dim sources (e.g., $I(\lambda) - I_{blackbody}(\lambda; T_{lattice}) \ll I_{blackbody}(\lambda; T_{lattice})$), the LED must only pump heat against a small temperature difference. As a result, efficiencies far in excess of unity are possible.

Examining an LED's behavior at fixed spectral intensity reveals another counter-intuitive aspect of the heat-pump regime. As the lattice temperature increases, the temperature difference against which the LED must pump becomes smaller, and the maximum allowable efficiency increases. Thus, the basic thermal physics of an LED in the heat pump regime is the reverse of the conventional thermal physics: above-unity efficiency results in self-cooling that decreases the device's operating temperature. For a desired spectral intensity, a higher lattice temperature means that the device can be more efficient. These differences may result in practical consequences for both the device-level design of LEDs and the thermal design of their packaging.

Electrons as the Working Fluid

FIG. 2 is a diagram, based on the Peltier effect, that illustrates entropy flow among a photon field 202, an electronic system 204, and a phonon field 206 of a conventional double hetero-junction LED 200. The photon field 202, electronic system 204, and phonon field 206 each act as energy and entropy reservoirs, with arrows indicating energy and entropy flow among the reservoirs. Per convention, "+" signs indicate holes, and "−" signs indicate electrons. The upper and lower dashed lines indicate the Fermi levels for the electrons and holes, respectively, and the upper and lower solid lines indicate the conduction and valence bands, respectively, as in a conventional band diagram.

For simplicity, consider the processes of carrier injection and recombination separately. When electrons flow from a metal contact 210a into a lightly n-doped semiconductor 220a, the average energy of the carriers involved in conduction increases from around the Fermi level to an energy above it. This increase in energy is supplied by lattice heat (phonon field 206) in steady state through the Peltier effect. Generalizing this principle and applying it to a conventional double hetero-junction LED suggests that as electrons flow from the negative contact 210a towards a typical recombination site in the active region, lattice heat is absorbed as the electron energy increases. Likewise, as holes enter the LED's p-doped semiconductor region 220b from a positive metal contact 210b and diffuse toward the recombination site, they too draw energy from the semiconductor lattice. Since the semiconductor lattice is a thermodynamic reservoir, this energy also has entropy associated with it. Thus, in forward bias, during injection the carriers absorb entropy and energy from the lattice with a flux proportional to the slope of the relevant band edge.

Similarly, recombination of the holes and carriers results in the flow of energy and entropy from the electron-hole system 204 to the photon field 204 and phonon field 206. Although recombination and generation events take place continually even when there is no current, the net recombination determines these flows.

As with the majority carriers in the doped regions, even when the device is off, the electrons and holes in the active region are perpetually experiencing generation and recombination as the result of their interaction with other reservoirs. These processes can be thought of in terms of the following stoichiometric equation:

$$e^- + h^+ \leftrightarrow U_{bandgap} \quad (6)$$

where $e^-$ is an electron, $h^+$ is a hole, and $U_{bandgap}$ denotes some excitation with energy (and other conserved quantities) equal to that of the electron-hole pair. As with a typical chemical reaction, the reactants and products are in equilibrium at some concentrations. When carriers are injected into the active region by a forward bias voltage, the concentration of electrons n and holes p exceeds these values (i.e., when np exceeds the squared intrinsic carrier concentration $n_i^2$). Net recombination occurs, and the reaction is driven from left to right.

Each time that an electron-hole pair is annihilated, both energy and entropy are removed from the electron and hole gases. That is to say, annihilation reduces the number of microscopic configurations in which the conduction and valence bands can be occupied. However, this entropy cannot disappear entirely as doing so would violate the Second Law of Thermodynamics. Instead, the entropy removed from the electronic sub-system (the degrees of freedom from excitations of the conduction and valence band states) is transported to another sub-system at the same location in the LED 200. The entropy's destination depends on the destination of the electron-hole pair's energy. As seen in FIG. 2, for non-radiative recombination, the destination is the lattice (phonon field 206). For radiative recombination, the destination is the photon field 202.

Now consider just the flows of entropy and energy between the photon field 202, electronic system 204, and phonon field 206 shown in FIG. 2 without the internal dynamics of the electronic system 204. For each quantum of charge that flows through the LED 204, one net recombination event occurs. The amount of entropy that enters and leaves the photon field 202 and the phonon field 206 can be determined from knowledge of the energy flows among the photon field 202, electronic system 204, and phonon field 206 combined with Equations (1) and (2). However, because the electronic sub-system 204 is not in equilibrium at any fixed temperature, it must be examined more closely.

The electronic sub-system 204 can be modeled as a two-level system under different excitation conditions. This model represents the electronic degrees of freedom at a single point in space, where $f_c$ is the occupancy probability for the higher energy state, $f_v$ is the occupancy probability of the lower state, and the states are separated by an energy $\Delta E$. In terms of these quantities, the system's total energy and entropy are:

$$U = f_c \cdot \Delta E + U_0 \tag{7}$$

$$S = -k_B[(f_c \ln f_c + (1+f_c)\ln(1-f_c)) + (f_c \leftrightarrow f_v)] \tag{8}$$

where $U_0$ is a constant. Defining a degree of freedom corresponding to excitation from the lower state to the upper state makes it possible to find the amount of entropy change in the system per unit energy change for distortions of this type. This ratio can be expressed as the inverse temperature $T^{-1}$ of the electronic system:

$$T^{-1} = \frac{\partial S}{\partial U} = \frac{\frac{dS}{df_c} - \frac{dS}{df_v}}{\frac{dU}{df_c} - \frac{dU}{df_v}} \tag{9}$$

$$\frac{dS}{df_c} = -k_B[\ln f_c + 1 - \ln(1-f_c) - 1] \tag{10}$$

$$= -k_B \ln\left(\frac{f_c}{1-f_c}\right) \tag{11}$$

$$T^{-1} = \frac{\partial S}{\partial U} = \frac{-k_B \ln\left(\frac{f_c}{1-f_c}\right) + k_B \ln\left(\frac{f_v}{1-f_v}\right)}{\Delta E}. \tag{12}$$

Constraining the probability for occupancy of either state $f_c + f_v$ to be 1 so that the Fermi level $E_F$ falls halfway between the states in energy, the equation above can be rearranged to recover the expression for Fermi-Dirac occupancy in equilibrium at temperature T:

$$\exp\left(\frac{\Delta E}{k_B T}\right) = \frac{f_v}{1-f_v} \cdot \frac{1-f_c}{f_c} = \left(\frac{1-f_c}{f_c}\right)^2 \tag{13}$$

$$\exp\left(\frac{\Delta E/2}{k_B T}\right) = \left(\frac{1}{f_c} - 1\right) \tag{14}$$

$$f_c = \left(\exp\left(\frac{E_{upper-state} - E_F}{k_B T}\right) + 1\right)^{-1} \tag{15}$$

The preceding result shows that inverse temperature of a Fermionic system, meaning the amount of entropy added to the system when a unit of energy is added, can be calculated from the occupation of the states. That is to say, two situations which are described differently have the same temperature if their occupancies are the same.

FIGS. 3A, 3B, and 3C illustrate a two-level system that exhibits different types of excitations. They show that excitations which lead to the same occupation of states have the same effective temperature T*. This two-level system represents an ensemble of homogeneous quantum dots, each with one low-energy electron state and one high-energy state as before, but each also possessing a lattice with temperature $T_{lattice}$. The total charge between the states is taken to be $f_c + f_v = 1$ to ensure charge neutrality. If the lattice temperature $T_{lattice}$ is kept at 300 K and no electrical excitation is applied, the statistical two-level system has a Fermi level at exactly halfway between the two states and the occupancies $f_c$ and $f_v$ can be determined by the Fermi-Dirac distribution as shown in FIG. 3A. In other words, in FIG. 3A, the electronic system is in equilibrium with a lattice whose temperature of 300 K.

Since a recombination event removes an electron from a higher energy state and places it in a lower energy state (and vice versa for a generation event), consider the degree of freedom corresponding to $f_c \to f_c + \delta f$ and $f_v \to f_v - \delta f$. This degree of freedom corresponds to excitations that retain charge neutrality.

FIGS. 3B and 3C show two different types of excitations that result in the same values of $f_c$ and $f_v$. In FIG. 3B, the electrical system has been taken out of equilibrium with the lattice by an applied voltage $qV = \Delta E/2$ More specifically, a Fermi-level separation has increased the occupancy of the higher-energy state and decreased the occupancy of the lower-energy state. Although the lattice temperature in FIG. 3B is still 300 K, the system's effective temperature T*, which indicates the ratio of entropy to energy in the electronic system, is 600 K. In FIG. 3C, the electronic system is again in equilibrium with the lattice, but the lattice is heated at 600 K. Although the excitation sources in FIGS. 3B and 3C are different, the occupancies $f_c$ and $f_v$ are identical, so the effective temperature T* is the same in both cases.

To see how the effective temperature T* relates to occupancy, consider the energy difference between each state and its quasi-Fermi level. In both FIGS. 3B and 3C, the energy difference (number of $k_B T$'s, where $k_B$ is Boltzmann's constant and T is the device temperature) between each state and its quasi-Fermi level has been halved. Consequently the Fermi-Dirac occupation of the states in both situations is equal (i.e., $f_c$ and $f_v$ are the same in both). Since the total entropy S and energy U of the electron-hole system are determined entirely by $f_c$ and $f_v$, these quantities are also equal. As a result, the effective temperature $T^* = (\partial S/\partial U)^{-1}$ with which the electron-hole system interacts through inter-band processes is also the same for the electrical (FIG. 3B) and thermal (FIG. 3C) excitation conditions.

From these examples, the effective temperature T* in a semiconductor whose quasi-Fermi levels are separated by an energy $\Delta E_F$ in a region with bandgap energy $E_{gap}$ can be expressed as:

$$T^* \equiv T_{lattice}\left(1 - \frac{\Delta E_F}{E_{gap}}\right)^{-1} \tag{16}$$

This expression can be used to simplify the internal dynamics of the electronic system into a simple thermodynamic model. For inter-band processes in which the electronic system loses energy to another reservoir (e.g., via recombination), the corresponding loss of entropy is determined by T* from Equation (16). By contrast, for the intra-band electron-phonon scattering processes that comprise thermally assisted injection, the amount of entropy exchanged during an energy exchange is given by $T_{lattice}$.

Modifying FIG. 2 by consolidating all flows of entropy together and including the corresponding flows of energy from the various sources yields the canonical diagram for a thermodynamic heat pump shown in FIGS. 1C and 1D. As electrons and holes are injected into the active region, they absorb heat from the phonons at $T_{lattice}$. When the electrons and holes undergo radiative recombination in the LED's active region, they deposit the absorbed heat into the photon field at temperature $T^* > T_{lattice}$. Thus the electrons and holes act as a working fluid in a heat pump operating between these two temperatures. Additionally, in the optically thick limit (i.e., when light rays travel many absorption lengths as they pass through the active region), the active region radiates like a blackbody with unity emissivity, so that $T_{photon}=T^*$. Finally, in this case of only radiative recombination, since no irreversible processes are taking place, the heat pump can be Carnot efficient.

Phonon-Recycling LEDs

Figure 4:
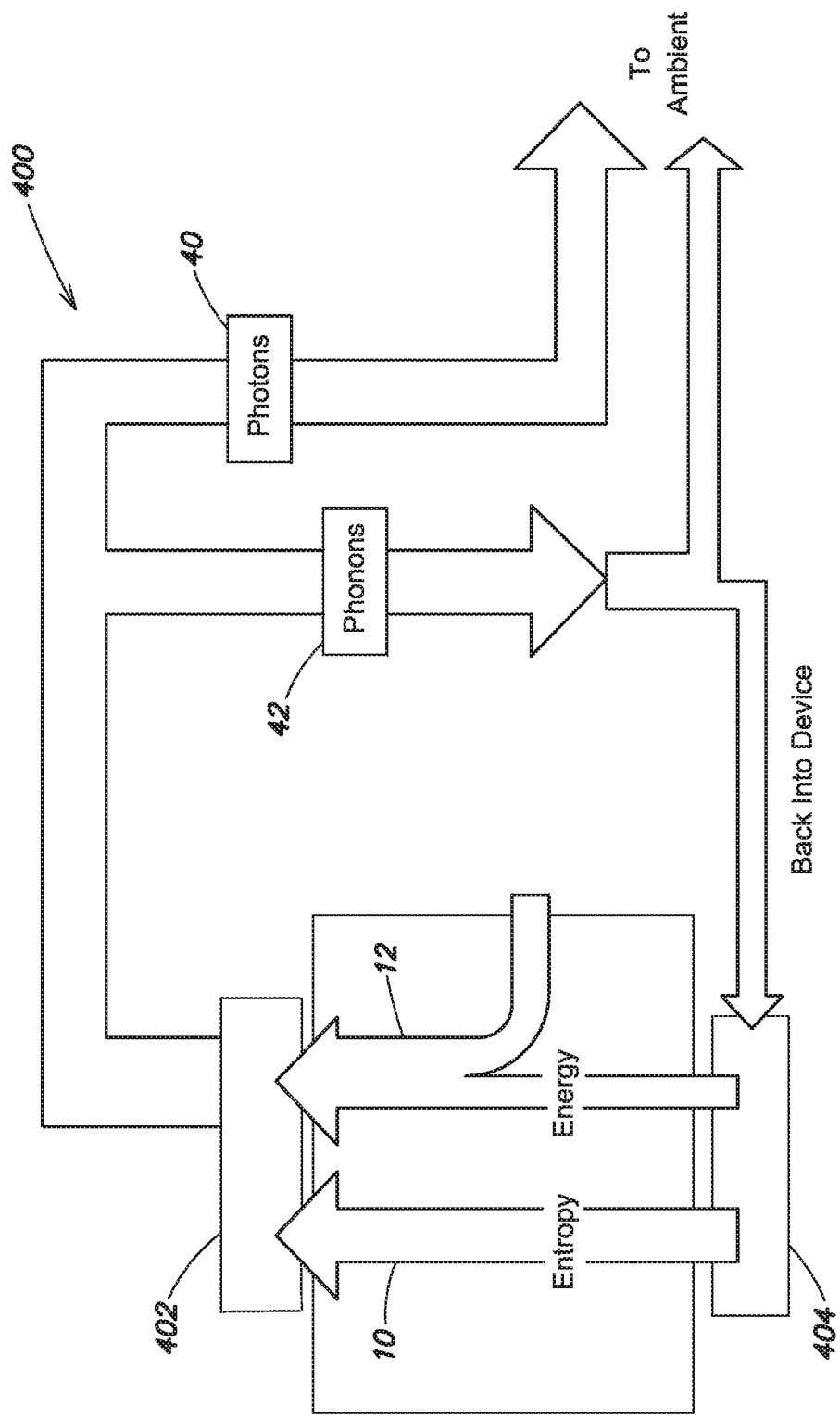
FIG. 4 depicts energy and entropy flows in a phonon-recycling LED.

FIG. 4 illustrates entropy and energy flows in an LED 400 operating as a phonon-recycling heat pump. As in FIGS. 1C and 1D, entropy 10 and energy 12 flow from a phonon field (lattice) 404 to a photon field 402. As in a conventional LED, the phonon-recycling LED 400 emits photons 40 from the photon field 402 into the environment ("to ambient"). In this case, however, the LED 400 also emits phonons 42, some of which propagate into the environment, and some of which are recycled back into the LED 400 via the phonon field 404. Recycling phonons 42 confines and concentrates heat within the LED 400, raising the LED's temperature (and hence the temperature of the lattice (phonon field 404)). Emitting phonons 42 into a high-temperature reservoir, such as the phonon field 404, also reduces the amount of entropy generated by the LED. For example, at 300 K, each 26 meV phonon carries away 1 $k_B$ of entropy, whereas at 900 K, each 26 meV phonon carries away ($\frac{1}{3}$) $k_B$ of entropy. Thus, concentrating heat chokes off entropy generation, thereby increasing the LED's efficiency.

Figure 5:
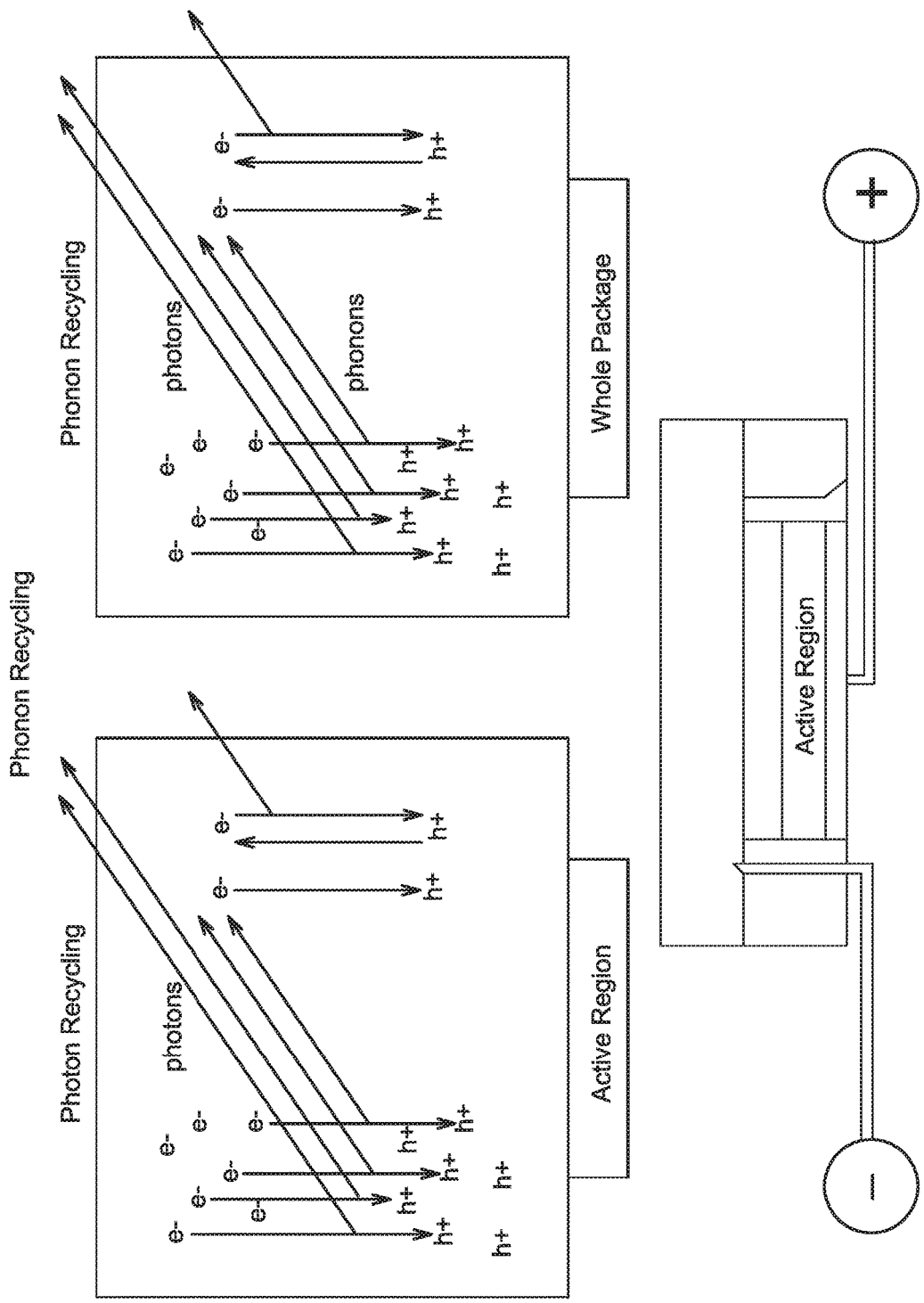
FIG. 5 depicts photon recycling (left) and phonon recycling (right) in an LED.

FIG. 5 illustrates differences between photon recycling (left) and phonon recycling (right) in an LED. In a photon recycling, photons are absorbed in the active region (intrinsic region of a PIN diode) to produce additional electron-hole pairs. In phonon recycling, phonons are absorbed throughout the PIN diode, including within the active region. This raises the temperature of the PIN diode's semiconductor lattice, promoting thermally assisted injection of electrons and holes into the active region.

Figure 6:
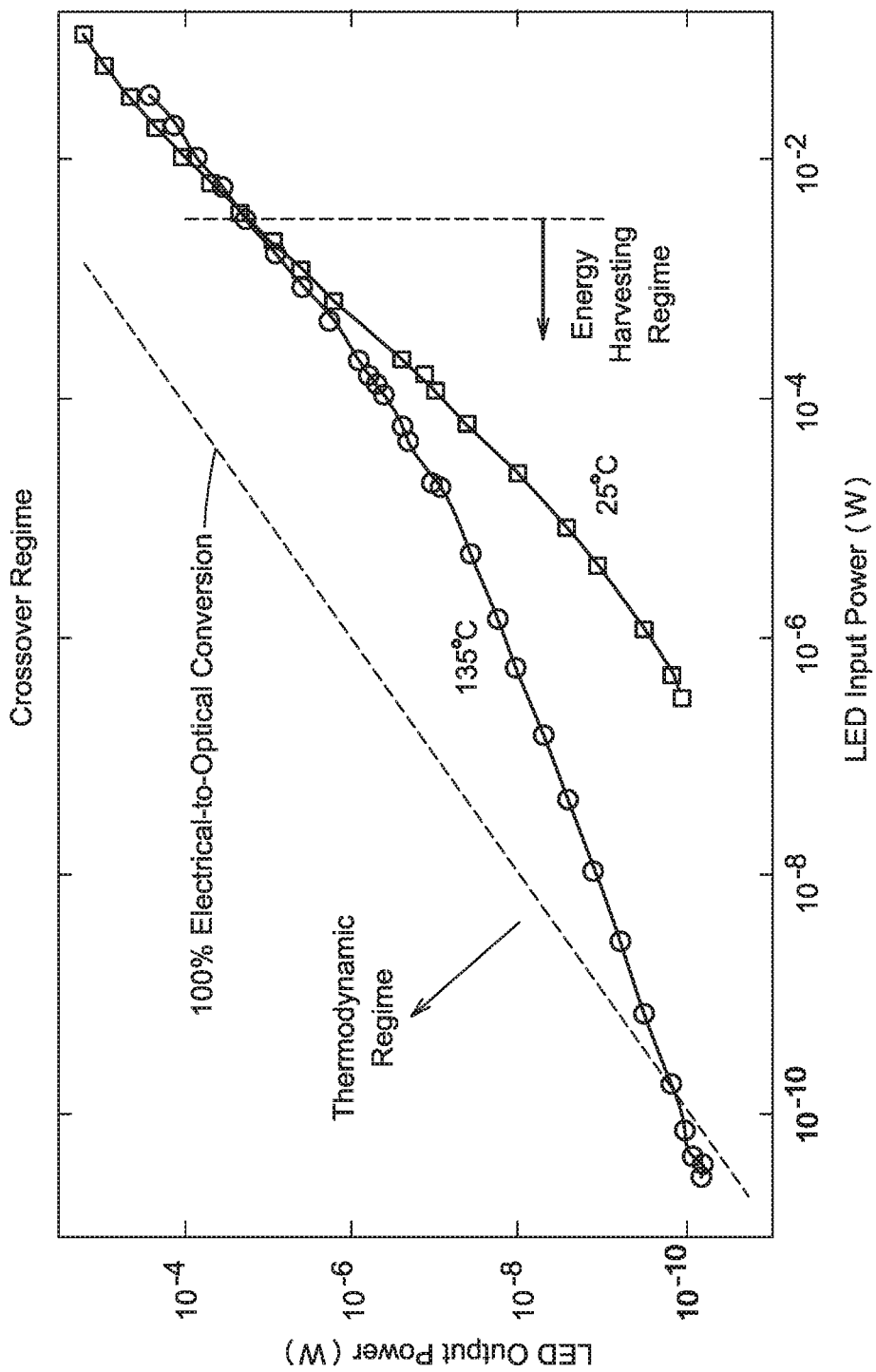
FIG. 6 is a plot of temperature versus efficiency at fixed power that illustrates stable thermal feedback loops for a thermo-electrically pumped LED.

FIG. 6 is a plot of LED output power versus LED output power that illustrates operation in the energy harvesting regime and the thermodynamic regime at different operating temperatures. The dashed diagonal line illustrates the "crossover"—100% electrical-to-optical conversion, or unity wall-plug efficiency—between the energy harvesting regime and the thermodynamic regime.

Figure 7:
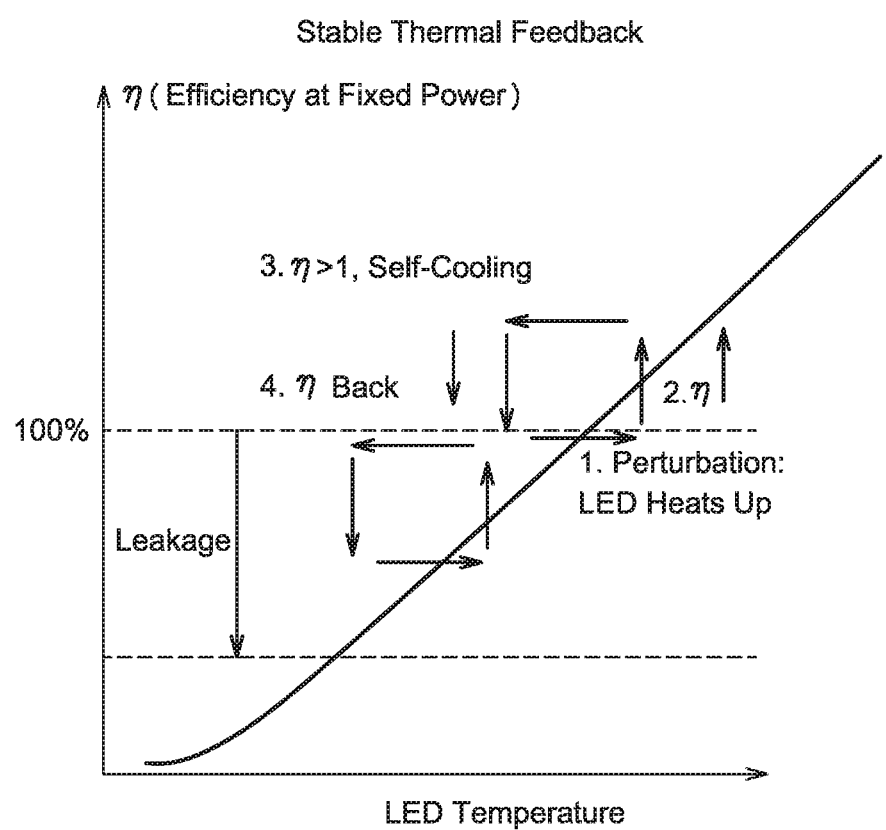
FIG. 7 is a plot of LED output power versus LED input power for the thermodynamic and energy harvesting regimes for an LED.

FIG. 7 is a plot of wall-plug efficiency η at fixed input power versus LED temperature for an LED that is perfectly thermally isolated from its surroundings. FIG. 7 also shows a pair of feedback loops that act to keep the LED in stable equilibrium at 100% wall-plug efficiency. Consider, for example, a perturbation that causes the LED to heat up is in the right-hand feedback loop. The increase in LED temperature causes the LED's efficiency to rise along the curve plotted in FIG. 7, which in turn causes electro-luminescent cooling. Cooling reduces the LED's temperature, so the LED returns to its equilibrium point. Similarly, a perturbation that causes the LED to drop in temperature produces a corresponding decrease in efficiency, which in turn causes the LED to heat up and increase in efficiency as in the left-hand feedback loop.

If heat leaks out of the system (i.e., if the system is not perfectly thermally isolated), however, then the LED may not remain in stable equilibrium at 100% wall-plug efficiency. Nevertheless, the LED should continue to exhibit stable feedback behavior despite energy loss. In fact, the overall efficiency at the stable feedback point, $\eta_s$, can be determined from the quality of heat confinement $K_{total}=K_{radiation}+K_{parasitic}$, where $K_{radiation}$ includes the electrical enhancement to blackbody radiation; the spectral efficiency of the radiation $S=P_{rad,useful}=P_{rad,total}$; and the external quantum efficiency, $\eta_{EQE}$, at the relevant bias voltage(s). The stable operating point is analogous to the unity efficiency operating point (where electro-luminescent cooling is seen) in externally heated low-bias LEDs, except that the heat is continuously supplied by the device's own inefficiency. The limit(s) on brightness at a given efficiency may be set by the temperatures at which the materials in use experience degradation.

Thermo-Electrically Cooled LEDs for Mid-Infrared Spectroscopy

Figure 8A:
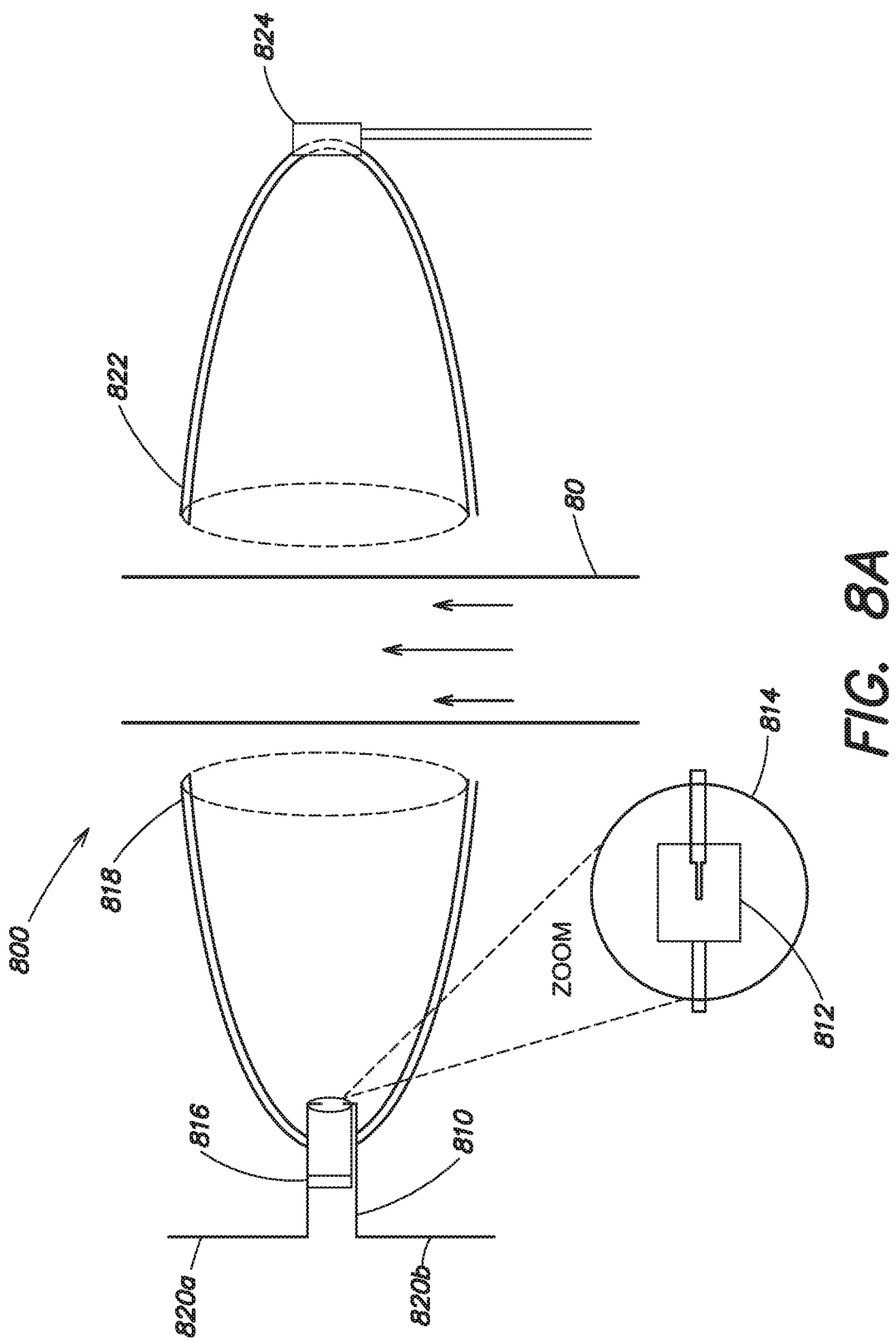
FIG. 8A illustrates a mid-infrared phonon-recycling LED used for down-hole spectroscopic analysis.

FIG. 8A shows a mid-infrared (mid-IR) spectroscopy system 800 suitable for down-hole spectroscopy, combustion exhaust analysis, and other similar applications. The system 800 includes a phonon-recycling LED 810 that transmits mid-IR light through a fluidic analyte 80, such as fluid produced from an oil well, to a photodetector 860, which generates a photocurrent whose amplitude represents the intensity of the transmitted light. A processor (not shown) coupled to the photodetector 860 may process this photocurrent to detect the presence or absence of $H_2S$, hydrocarbons (C—H bonds), and/or other substances in the fluidic analyte 80.

The LED 810 comprises a thin-film semiconductor diode structure (including an active region) 812 made of a semiconductor material (e.g., GaSb, InAs) selected to emit light at a mid-IR wavelength (e.g., 2-7 microns, 3-4 microns, around 3.5 microns, around 4.23 microns, etc.) with relatively high quantum efficiency (e.g., 70%, 75%, 80%, 85%, 90%, 95%, etc.). The diode structure 812 may be configured for low-bias operation, e.g., at a bias voltage of less than about 0.19 V to about 0.62 V for mid-IR emission (e.g., less than about 0.60 V, 0.55 V, 0.50 V, 0.45 V, 0.40 V, 0.35 V, 0.30 V, 0.25 V, 0.20 V, 0.15 V, 0.10 V, or 0.05 V). In some cases, the diode structure 812 may be doped to raise the low-bias external quantum efficiency $\eta_{EQE}$ and therefore the optical power density available without net heat generation. The diode structure 812 may also include or be in thermal and/or optical communication with a microstructure that increases heat transfer to and/or photon extraction from the active region. Moreover, reducing the ratio $E_{gap}/k_BT$ may produce further increases in power density.

FIG. 8A shows that the diode structure 812 is mounted on a transparent thermal insulator 814, which in turn is mounted or affixed to a reflector 816. Conductive wires (electrical leads) 820a and 820b extend from electrical contacts on either side of the diode structure's active region. And a reflective collimating element 818, such as a Winston cone (an off-axis parabola of revolution), extends around the LED 810 along an axis orthogonal to the predominant flow direction of a fluidic analyte 80, which may be a fluid stream or jet.

In operation, the wires 820a and 820b conduct current through the diode structure 812 so as to cause the diode structure 812 to emit mid-infrared light. Some of this light propagates directly through the fluidic analyte 80; some light reflects off the reflective collimating element 818, which redirects the reflected light so as to form a collimated beam propagating towards the fluidic analyte 80; and some light may propagate towards transparent thermal insulator 814. The transparent thermal insulator 814, in turn, transmits some of this light to the reflector 816, which reflects incident light back towards the fluidic analyte 80, possibly via the reflective collimating element 818.

Figure 8B:
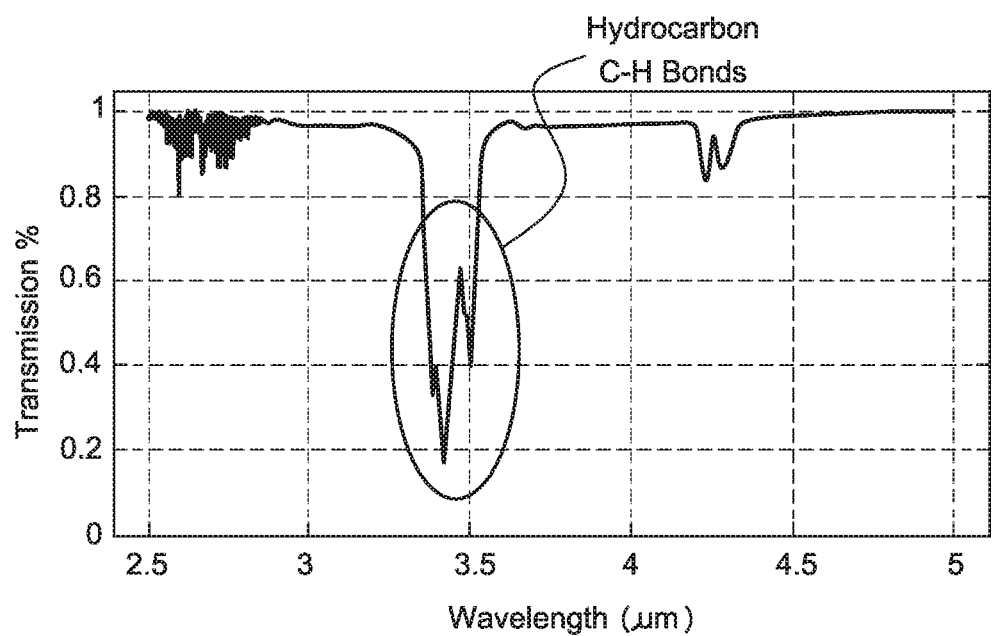
FIG. 8B is a plot of the absorption spectrum of hydrocarbon C—H bonds.
Figure 8C:
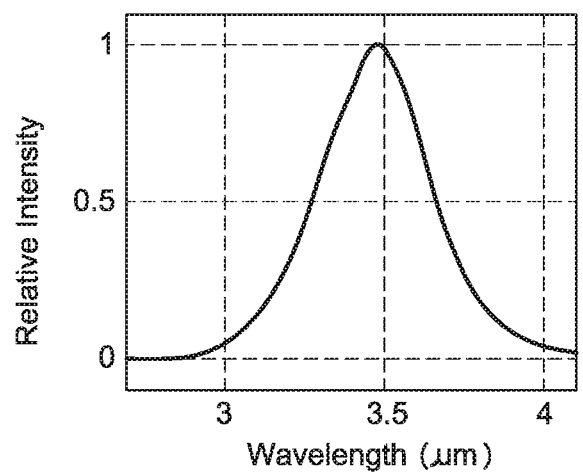
FIG. 8C is a plot of the emission spectrum of the mid-infrared phonon-recycling LED shown in FIG. 8A.

Depending on its composition, the fluidic analyte 80 may absorb some or all of the incident mid-IR light. For example, if the fluidic analyte 80 comprises a compound with hydrocarbon C—H bonds, its absorption spectrum may resemble the transmittance versus wavelength plot shown in FIG. 8B, with nearly 80% absorption at a wavelength of about 3.4 μm. And if the LED's emission spectrum is as shown in FIG. 8C, with an emission peak at about 3.5 μm with a full-width half-maximum of about 0.5 μm, then the fluidic analyte 80 may strongly absorb the light emitted by the LED 810. If the fluidic analyte 80 does not absorb the light emitted by the LED 810, e.g., because it does not have any (or many) hydrocarbon C—H bonds, then it may transmit some or all of the light emitted by the LED 810.

A second Winston cone 822 focuses the light transmitted by the fluidic analyte 80 onto a mid-IR photodetector, which produces a photocurrent or other signal representative of the irradiance of the detected light. If the fluidic analyte 80 absorbs light strongly, then the photocurrent may be low; otherwise, the photocurrent may be high. A processor (not shown) operably coupled to the photodetector 824 may sense the photocurrent and provide an indication of the presence or absence of a particular compound (e.g., a hydrocarbon) based on the photocurrent's amplitude. For example, the processor may use the photocurrent to determine a gas/oil ratio (GOR) of the fluidic analyte 80 or to analyze the composition of combustion exhaust.

Unlike in a conventional LED, which may include a heat sink to dissipate heat generated by the active region, the transparent thermal insulator 814 thermally isolates the diode structure 812, causing heat generated by the diode structure 812 to remain confined to the diode structure 812. In some cases, the insulator 814 may be configured to concentrate this recycled heat to a certain portion of the diode structure 812. By preventing heat from flowing out of the diode structure 812, the insulator 814 causes the diode structure 812 to heat up during operation. Increasing the diode structure's temperature promotes thermally assisted injection of holes and electrons into the active (intrinsic) region of the diode structure 812 as described above. Due to this thermally assisted injection, the LED 810 may operate with a wall-plug efficiency of over 100%, which is several orders of magnitude higher than the 0.1% to 1.0% wall-plug efficiencies of conventional mid-IR LEDs.

In addition, unlike a conventional LED, the mid-IR LED 800 does not necessarily have to be cooled when operated in a high-temperature environment, such as in the exhaust stack of a combustion engine. In some embodiments, the LED 800 may be configured to absorb heat, further increasing efficiency as well as potentially easing constraints on operating temperature and LED cooling. Conversely, conventional mid-IR LEDs tend to operate less efficiently with increasing temperature.

In some respects, the LED 810 shown in FIG. 8A is a hybrid device whose mechanical design resembles that of a thermal source (blackbody radiator) and whose electronic design resembles that of a conventional LED. Because the LED 810 resembles both a thermal source and a conventional LED, it operates at relatively high efficiency (e.g., greater than 50% efficiency) and the intensity of its emission can be modulated rapidly. As a result, it can outperform both thermal emitters and conventional LEDs in infrared spectroscopy.

Thermo-Electrically Cooled LEDs for Optical Communication

Figure 9:
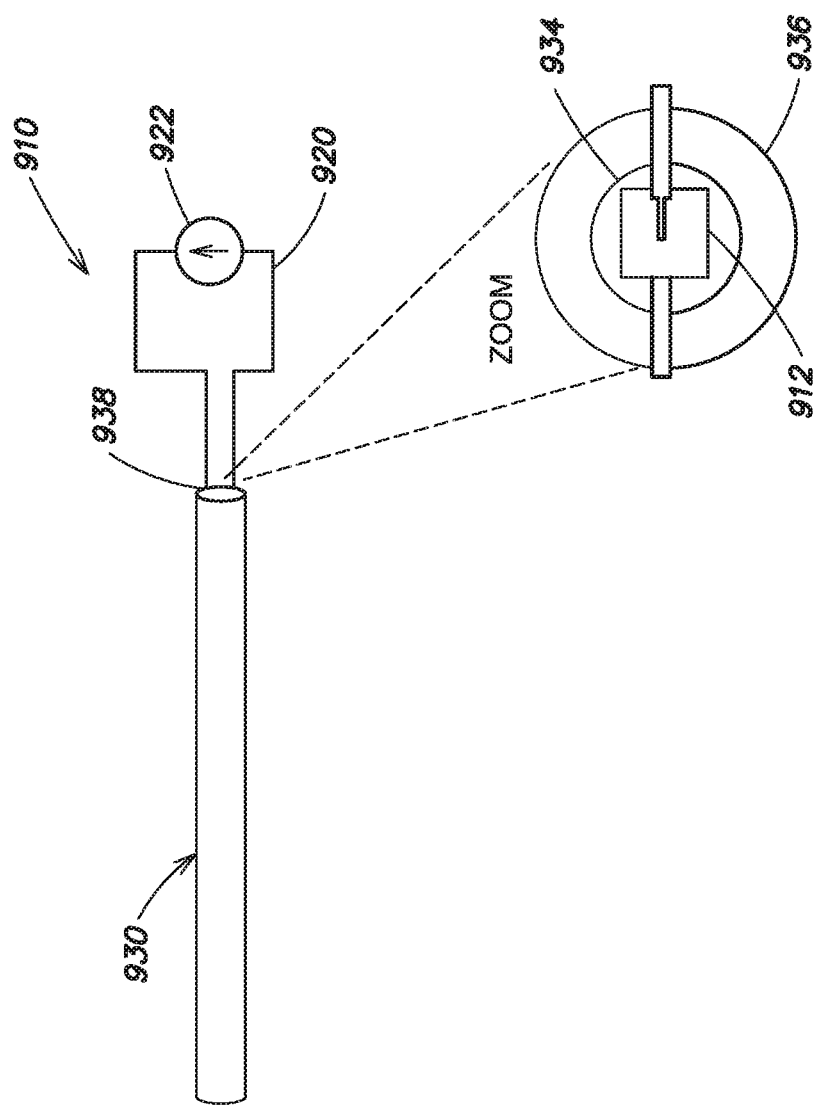
FIG. 9 illustrates a fiber-coupled phonon-recycling LED suitable for optical communications and/or fiber-based illumination.

FIG. 9 illustrates a thermo-electrically cooled LED 910 at one end of an optical fiber 930 for use in an optical communications system or fiber-optic illumination system. The LED 910 includes a thin-film semiconductor diode structure (e.g., a homojunction or heterojunction diode) 912 that is optically coupled to a cleaved facet 938 at one of the fiber 930. In some embodiments, the diode structure 912 (also known as an active region) is bonded (e.g., using epoxy) or otherwise affixed to the fiber 930. A conductive wire 920 provides an electrical connection between the diode structure 912 and a current source 922 used to power the LED 910. The LED 910 may be configured to operate at low bias (e.g., at a bias voltage corresponding to an energy below the photon energy). For instance, the bias voltage may be less than about 0.70 V to about 1.0 V (e.g., less than about 0.90 V, 0.80 V, 0.70 V, 0.60 V, 0.50 V, 0.40 V, and so on) for operation in the telecom bands at 1310 nm and/or 1550 nm.

In operation, electrons and holes recombine in the LED's active area (not shown) to produce near-infrared light (e.g., at about 1310 nm or about 1550 nm) for optical communications or visible light for fiber-optic illumination. At least some of the light emitted by the LED 910 enters the fiber's core 934, which is surround by a cladding 936 (and possibly one or more buffer layers (not shown)). Depending on the differences in refractive indices of the core 934 and cladding 936, the core diameter, and the wavelength of light emitted by the LED 910, the fiber 930 may guide light in a single transverse mode or multiple transverse modes. Modulating the intensity of the light emitted by the LED 910, e.g., with a signal source (not shown) coupled to the current source 922, produces an optical signal that can be detected with a detector (not shown) optically coupled to the far end of the fiber 930. As well understood by those of skill in the art, the LED 910 can be modulated according to any suitable modulation scheme over bandwidths of up to 1 GHz (e.g., 100 MHz, 250 MHz, 500 MHz, and so on).

FIG. 9 also shows that the LED 910 is not heat sunk. As a result, the LED 910 tends to heat up during operation, which in turn causes the LED's wall-plug efficiency to increase. For example, the LED 910 may become hotter than the current source 922 during operation. Indeed, waste heat from the current source 922 could be used to heat the LED 910.

Thermo-Electrically Cooled LEDs for Illumination

Figure 10:
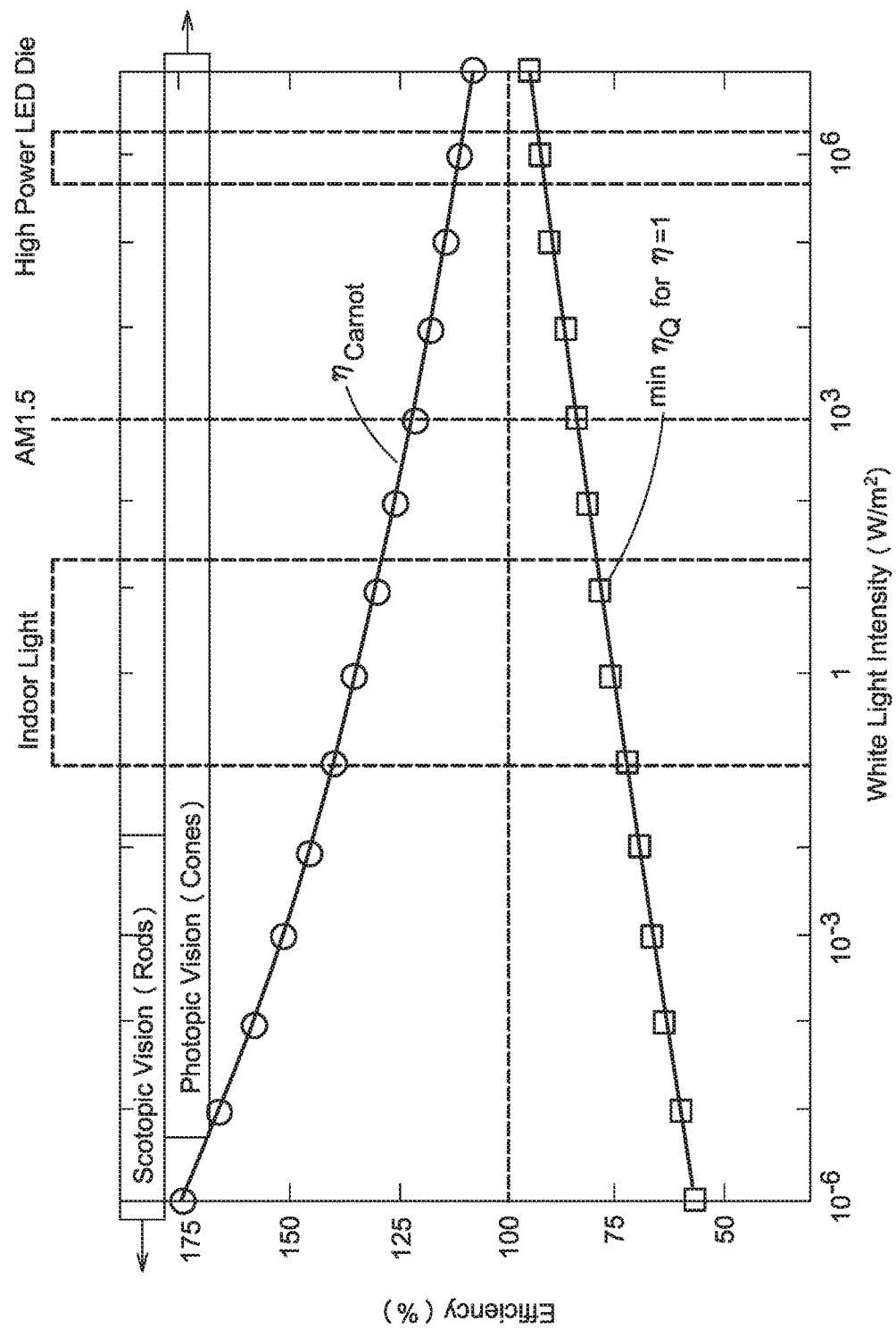
FIG. 10 is a plot of efficiency versus white light intensity for LEDs with different quantum efficiencies.

FIG. 10 is a plot of wall-plug efficiency versus white light intensity. The horizontal dashed line indicates 100% wall-plug efficiency, the dotted line with squares indicates the minimum quantum efficiency to achieve 100% wall-plug efficiency, and the solid line with circles indicates the Carnot efficiency limit. Typically, indoor lighting has an intensity of about 0.1 W/m$^2$ to about 10 W/m$^2$, whereas a high-power LED die may operate with an intensity of about 10$^6$ W/m$^2$. By comparison, phototopic vision in an average human begins at intensities of about 10$^{-6}$ W/m$^2$.

FIG. 10 shows that the minimum quantum efficiency $\eta_Q$ (dotted line with squares) for a semiconductor material used in a unity-efficiency, phonon-recycling LED for indoor lighting is about 75%. As understood by those of skill in the art, the material quantum efficiency can be altered (and possibly increased) by doping the material, varying the doping profile, minimizing defects, or changing its structure (e.g., to form quantum dots, periodic structures, homojunctions, heterojunctions, etc.). For instance, the LED's microstructure may be engineered to improve heat transfer and photon extraction.

Figure 11A:
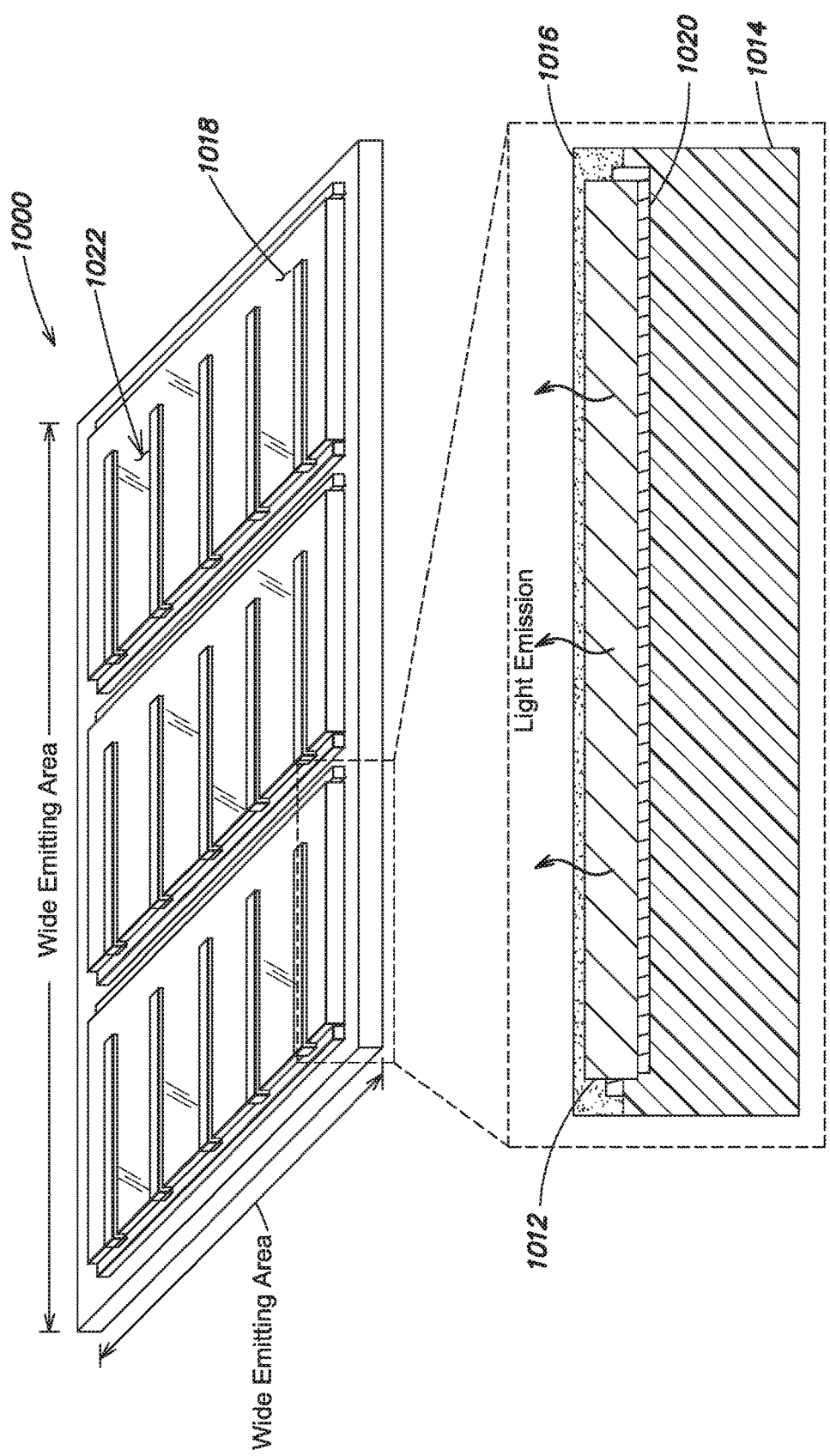
FIG. 11A illustrates a wide-area phonon-recycling LED suitable for ambient illumination.
Figure 11B:
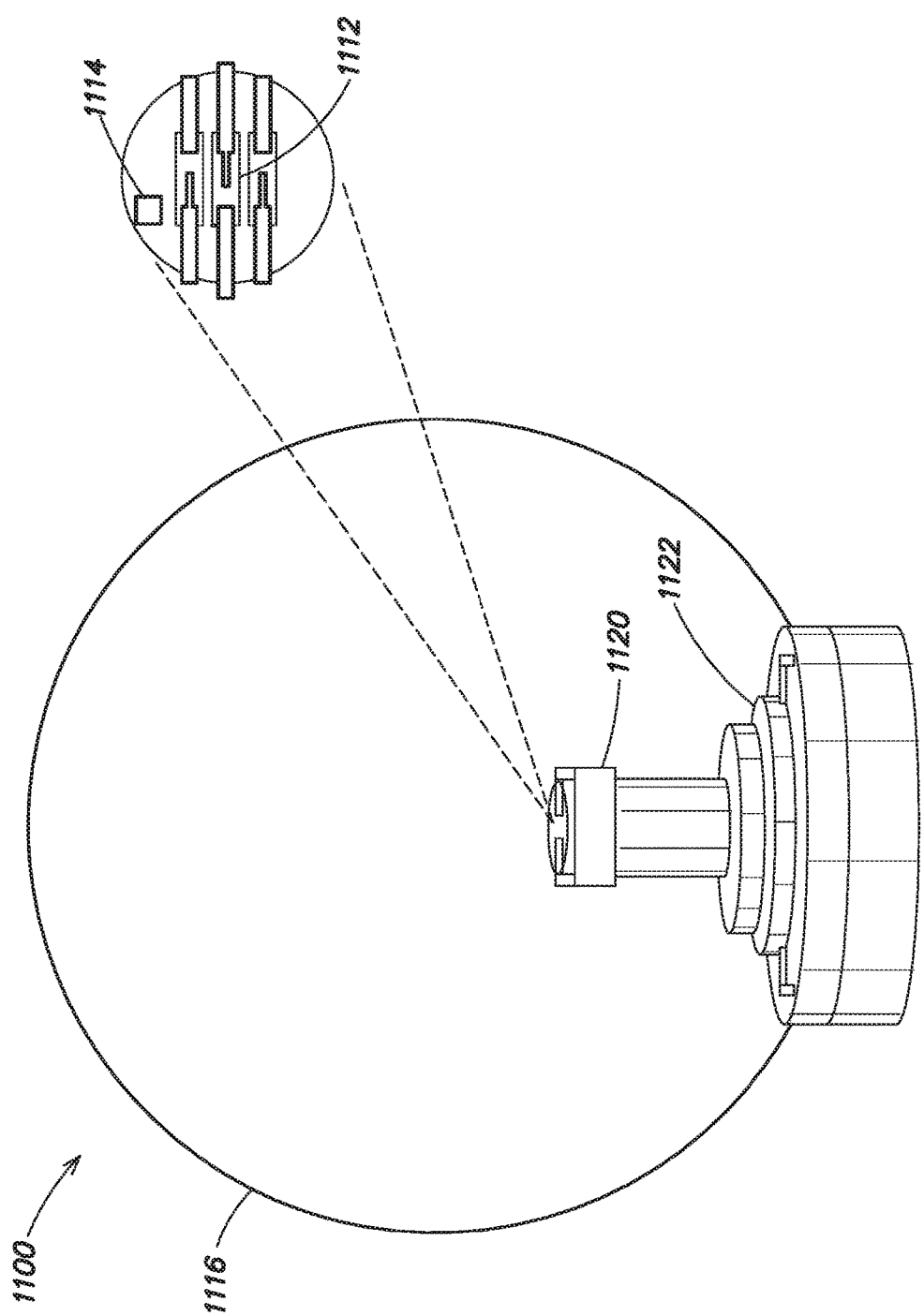
FIG. 11B illustrates a phonon-recycling LED with a thermally isolated filament.

FIGS. 11A and 11B illustrate phonon-recycling LEDs for low-brightness illumination, ambient illumination, displays, etc. FIG. 11A shows a LED lighting panel 1000 suitable for providing wide-area illumination. The LED lighting panel 1000 includes one or more large-area semiconductor diodes (active regions) 1012, each of which is coated on one side with a reflective back contact 1020 and on the other side by a transparent front contact 1022 (e.g., made of indium tin oxide or any other suitable material). If desired, the diode structure(s) 1012 can be coated or encased in a transparent encapsulant 1016 that protects the light-emitting surface(s) of the semiconductor diode(s) 1012 from scratches and nicks and textured to form an optional textured emitting surface 1018 that scatters or diffuse light emitted by the diode structure(s) 1012.

Unlike in conventional LEDs, which are usually mounted on heat sinks to dissipate internally generated heat, the diode structure 1012 is mounted on a thermally insulating substrate 1014. For instance, the semiconductor diode(s) 1012 can be made using any suitable technique, including epitaxial lift-off, in which case one or more diode structures 1012 are grown epitaxially on a sacrificial substrate, then removed from the substrate and mounted or affixed to a high-temperature, thermally insulating substrate 1014 (e.g., an oxide- or polymer-based substrate).

In operation, the LED lighting panel 1000 is biased at low bias. The exact bias voltage V depends on the emission wavelength, and can be chosen such that $qV < \hbar\omega$. For visible light emission, the bias voltage may be less than about 1.75 V to about 3.25 V (e.g., less than about 3.2 V, 3.1 V, 3.0 V, 2.9 V, 2.8 V, 2.7 V, 2.6 V, 2.5 V, 2.4 V, 2.3 V, 2.2 V, 2.1 V, 2.0 V, 1.9 V, 1.8 V, 1.7 V, 1.6 V, 1.5 V, 1.4 V, and so on). When the LED lighting panel 1000 is on, the diode structure 1012 generates excess heat, and the thermally insulating substrate 1014 traps a substantial amount of this heat in the diode structure 1012. By trapping (rather than dissipating) heat in the diode structure 1012, the thermally insulating substrate 1014 increases the LED lighting panel's efficiency as explained above.

FIG. 11B shows a phonon-recycling LED light bulb 1100. Like a conventional light bulb, the LED light bulb 110 includes a "filament"—in this case, a multi-phase LED load 1112—suspended in a thermally insulating gas-filled bulb 1116. The multi-phase LED load 1112 is biased at low bias, e.g., at any value less than about 1.75 V to less than about 3.25 V for visible light emission. Applying an alternating current to a primary coil 1122 at the base of the LED light bulb 1100 induces a current in a secondary coil 1120 coupled to a power conditioning unit 1114, which applies a conditioned version of the induced current to the multi-phase LED load (active region) 1112. The current causes the LED load 1122 to emit light and generate heat. Because the LED load 1122 is mounted within a thermally insulating gas-filled bulb 1116, however, the heat that it generates cannot dissipate easily. Instead, the heat remains confined within the LED load 1122 to raise the LED load's operating temperature.

EXEMPLIFICATION

The following example is intended to illustrate aspects of the present disclosure without limiting the appended claims.

As explained above, the presence of entropy in incoherent electromagnetic radiation permits semiconductor light-emitting diodes (LEDs) to emit more optical power than they consume in electrical power, with the remainder drawn from lattice heat. The experimental results in FIGS. 13-15 show electro-luminescence, in a conventional LED (illustrated in FIG. 12), in which the ratio of detected optical power to supplied electrical power, known commonly as the wall-plug efficiency $\eta$ (or as the heating coefficient of performance), exceeds unity. These experimental results illustrate the potential of phonon-recycling to increase efficiency in both LED lighting and solid-state cooling.

The experimental results shown in FIGS. 13-15 were achieved by exploring a regime where the active region carrier concentrations n and p did not always exceed the intrinsic concentration $n_i$. The forward bias applied to the LED was about V=70 µV, so that qV was several hundred times smaller than $k_B T$. At bias voltages $V < k_B T/q$, sometimes referred to as the low-bias regime, quantum efficiency $\eta_{EQE}$ became voltage-independent. Despite quantum efficiencies as low as $\eta_{EQE} \approx 3 \times 10^{-4}$, the results show both net electro-luminescent cooling and wall-plug efficiency $\eta$ (the ratio of collected light power to input electrical power) that exceeded 200%. Further reductions in the bias voltage led to further increases in the wall-plug efficiency $\eta$. In addition, moving to LED materials with narrower bandgaps (smaller $E_{gap}$) and raising the emitter lattice temperature increased the power available in the low-bias regime by several orders of magnitude.

Figure 12:
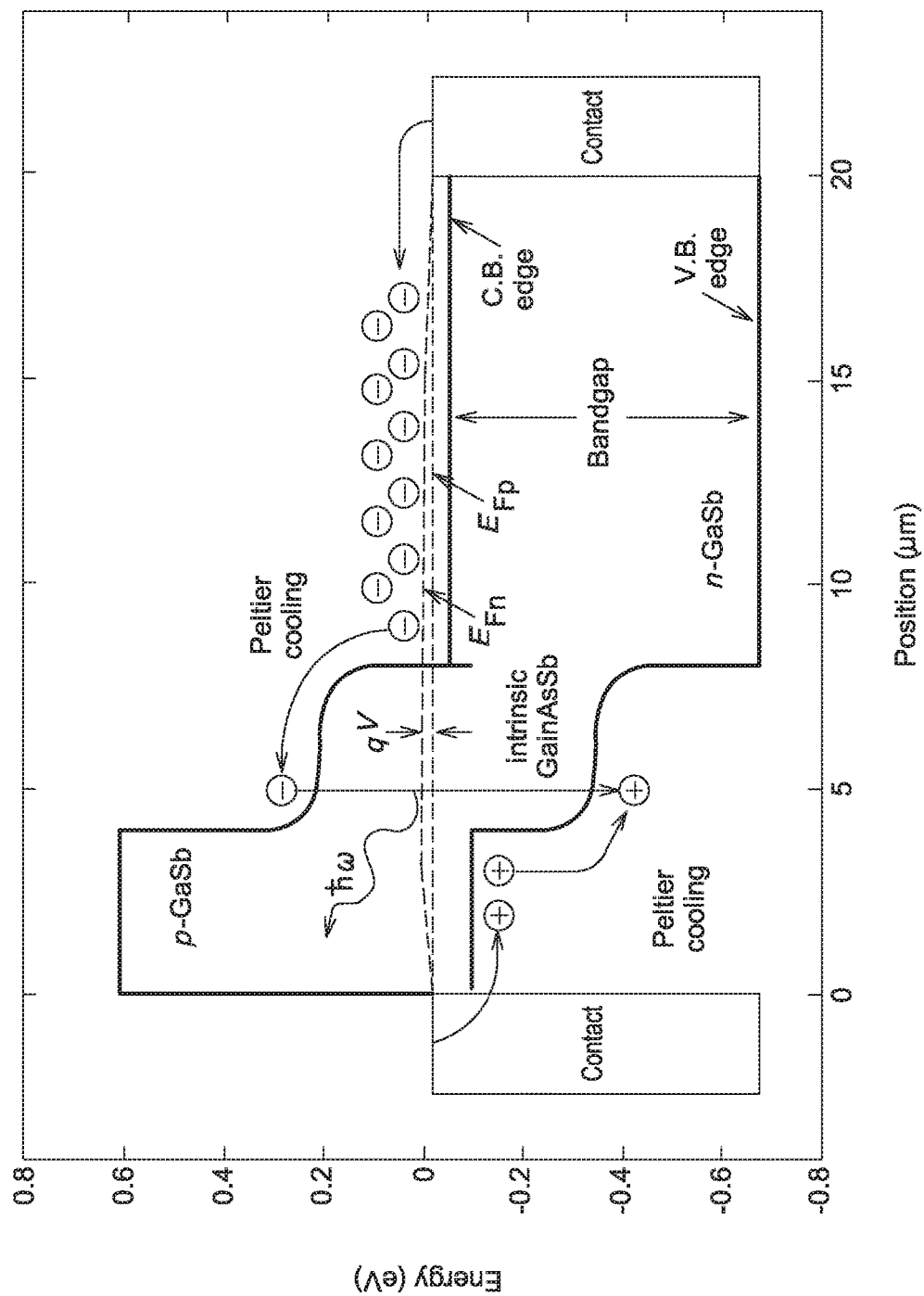
FIG. 12 is a band diagram of a double-heterostructure LED operating at low bias in the "heat pump" regime.

FIG. 12 is a band diagram of the double hetero-junction LED used to produce the experimental results described here at a forward bias of 26 mV. Peltier cooling occurred at the contacts on either end of the LED and at the intrinsic GaInAsSb active region in the middle of the LED. Applying a small forward bias (e.g., the 26 mV shown in FIG. 12) caused the LED to act as a heat pump: it drew energy from the lattice to inject electrons and holes from the n- and p-doped GaSb regions, respectively, into the active region. The injection process drove both radiative recombination, which caused light emission, and non-radiative recombination, which promoted thermally assisted injection of electrons and holes. At low bias, these processes resulted in a small but measurable forward current and net outgoing photon flux.

During the experiments, the LED was heated to temperatures ranging from 25° C. to 135° C. When the LED was heated to 135° C., it emitted light at a center wavelength of about 2.42 µm with a full-width half maximum of about 0.29 µm as well as up to about 40 nW of blackbody radiation. Below optical output powers of approximately 1 µW, the optical output power was measured using a lock-in technique. The LED was placed electrically in series with an unheated resistor and the combined load was biased with a 1 kHz on-off voltage square wave. This resistor dominated the load across the function generator so that the LED was approximately current biased. The optical power was detected by a long-wavelength InGaAs p-i-n photo-diode whose photo-current signal was amplified and measured by a trans-impedance amplifier connected to a digital lock-in amplifier. The phase of the optical power signal remained fixed as the excitation voltage was reduced, indicating that even at low power the measured signal was the result of LED electro-luminescence. The uncertainties presented result primarily from background electrical noise in the lock-in measurement of optical power. This noise was observed to be zero-mean, with no preferential phase relationship to the excitation signal. The phase of the optical power signal remained fixed as the excitation voltage was reduced. Above 100 nW, an overlapping power measurement was made using a DC voltage source and digital multimeter. The lock-in optical power measurements agreed with the DC measurements to within the experimental uncertainty.

The curve fits (lines) shown alongside the experimental data in FIGS. 13-15 were produced using a one-dimensional simulation of the first three moments of the Boltzmann Transport Equation, a lattice heat diffusion equation, and an optical transmission calculation. The carrier transport equations were solved self-consistently with the lattice heat diffusion equation using a commercial software package. The recombination mechanisms in the carrier transport model were bulk trap-based Shockley-Read-Hall (SRH) recombination, surface SRH recombination at the hetero-interfaces, radiative bimolecular recombination, Auger recombination, and surface recombination at the contacts. The optical transmission calculation was used to correct for the effects of photon recycling and changes in extraction at high bias. The simulation included three fitting parameters: a series contact resistance of 0.779Ω, a non-radiative bulk SRH lifetime at 300 K of 95 ns, and a collection efficiency of 24.5% used in the simulation. This collection efficiency indicates that the experimentally measured 231% wall-plug efficiency corresponds to a simulated internal wall-plug efficiency of 943%.

Figure 13A:
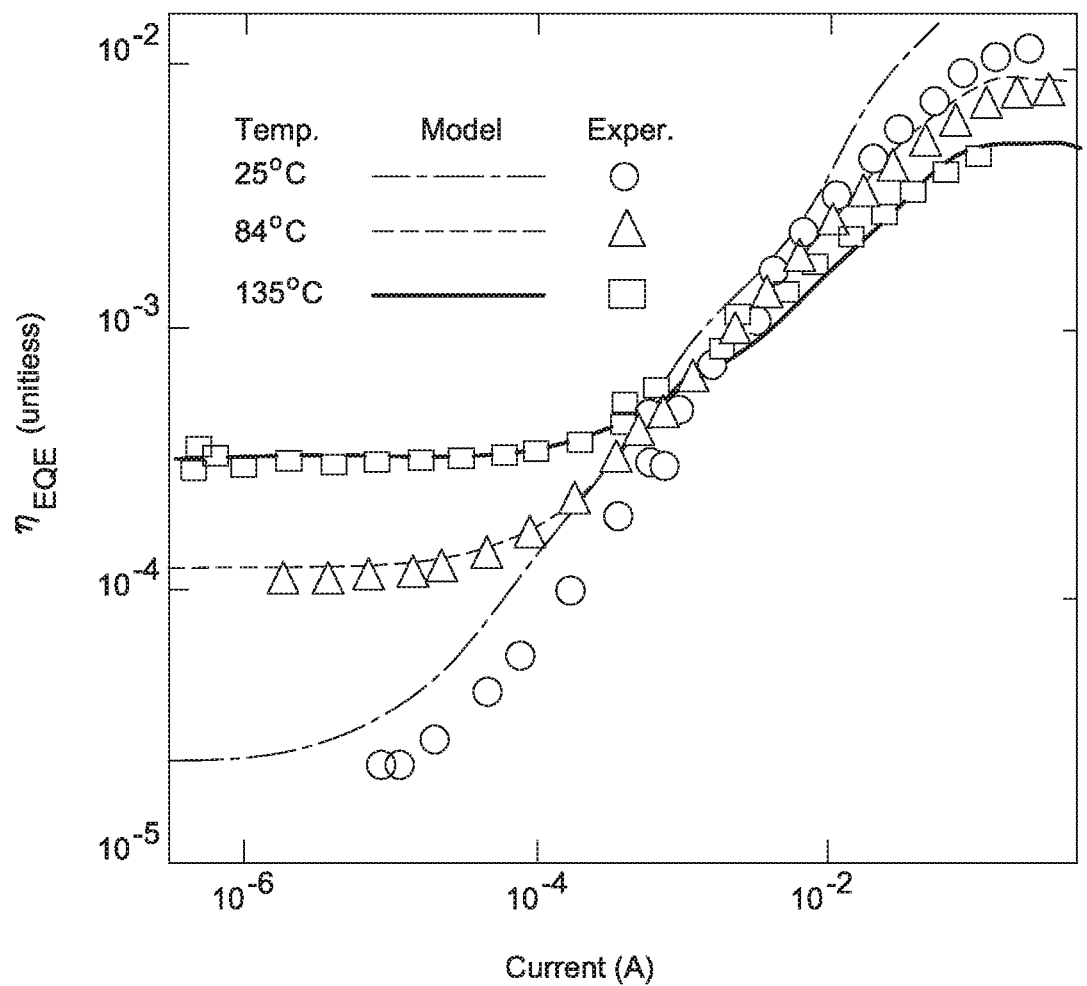
FIGS. 13A and 13B are plots of external quantum efficiency versus current and bias voltage, respectively, for the LED of FIG. 12 operating at different temperatures.
Figure 13B:
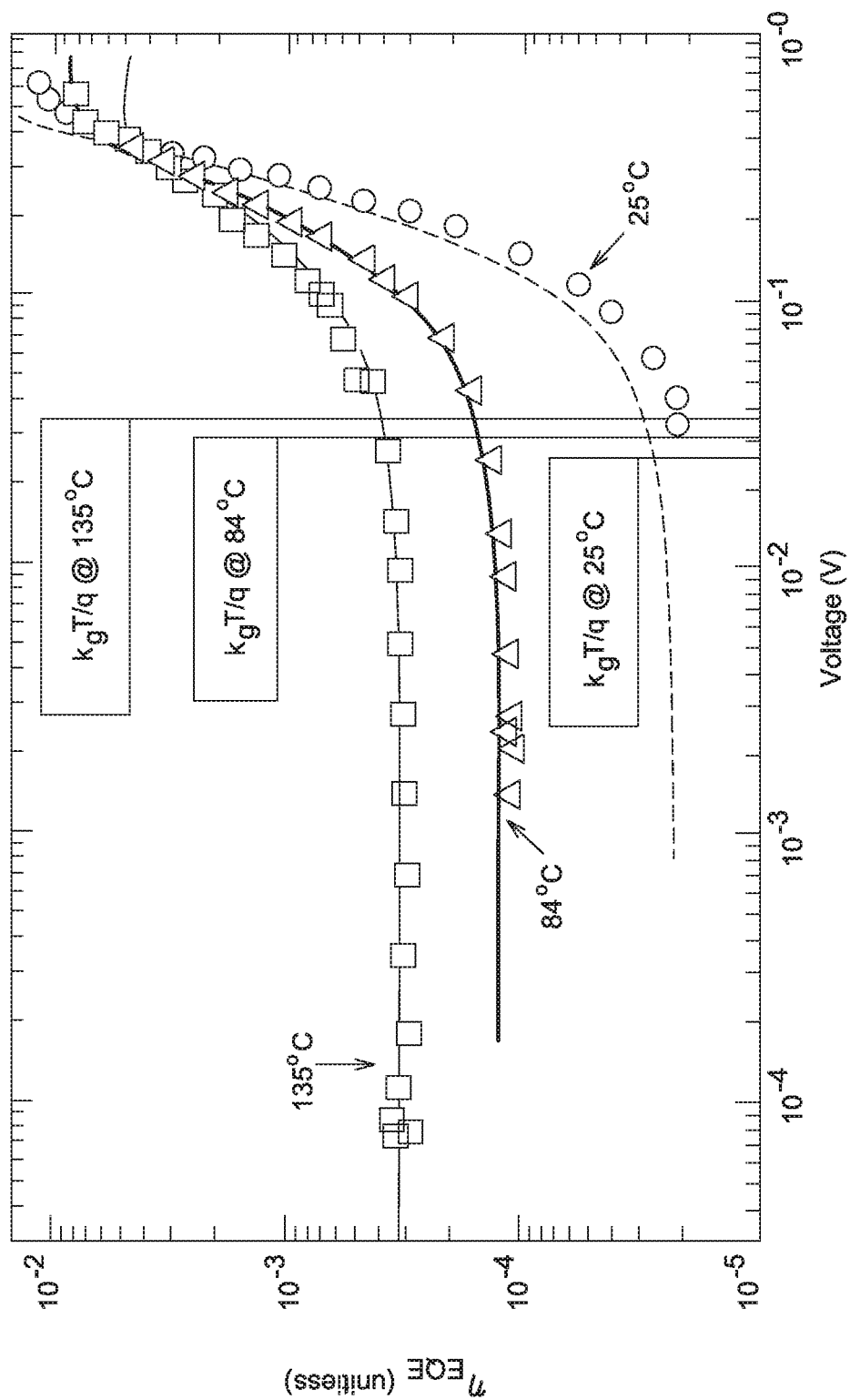

FIGS. 13A and 13B are plots of the quantum efficiency $\eta_{EQE}$ versus current and voltage, respectively, in the low bias regime. Markers represent measurements at operating temperatures of 25° C., 84° C., and 135° C., and lines indicate the corresponding simulations. The plots show that the quantum efficiency is independent of current and voltage at sufficiently low bias. Without being bound by any particular theory, bias voltages of $V \ll k_B T/q$ constitute a small deviation from thermodynamic equilibrium and drive net photon generation as a linear response in much the same way as a small excess of reactants drives a chemical reaction. Applying a forward bias raises the steady-state concentration of electrons no and holes $p_0$ by $\delta n$ and $\delta p$, respectively. The total radiative recombination rate is proportional to the product np, where $n = n_0 + \delta n$ and $p = p_0 + \delta p$. Since recombination balances generation at equilibrium, the cross-terms of this product give the net recombination rate to leading order in the deviations $\delta n$ and $\delta p$. Since net light emission is linearly proportional to $\delta n$ and $\delta p$, and $\delta n$ and $\delta p$ are linear in V, at low bias an LED's quantum efficiency is finite, including as V approaches zero.

Figure 13C:
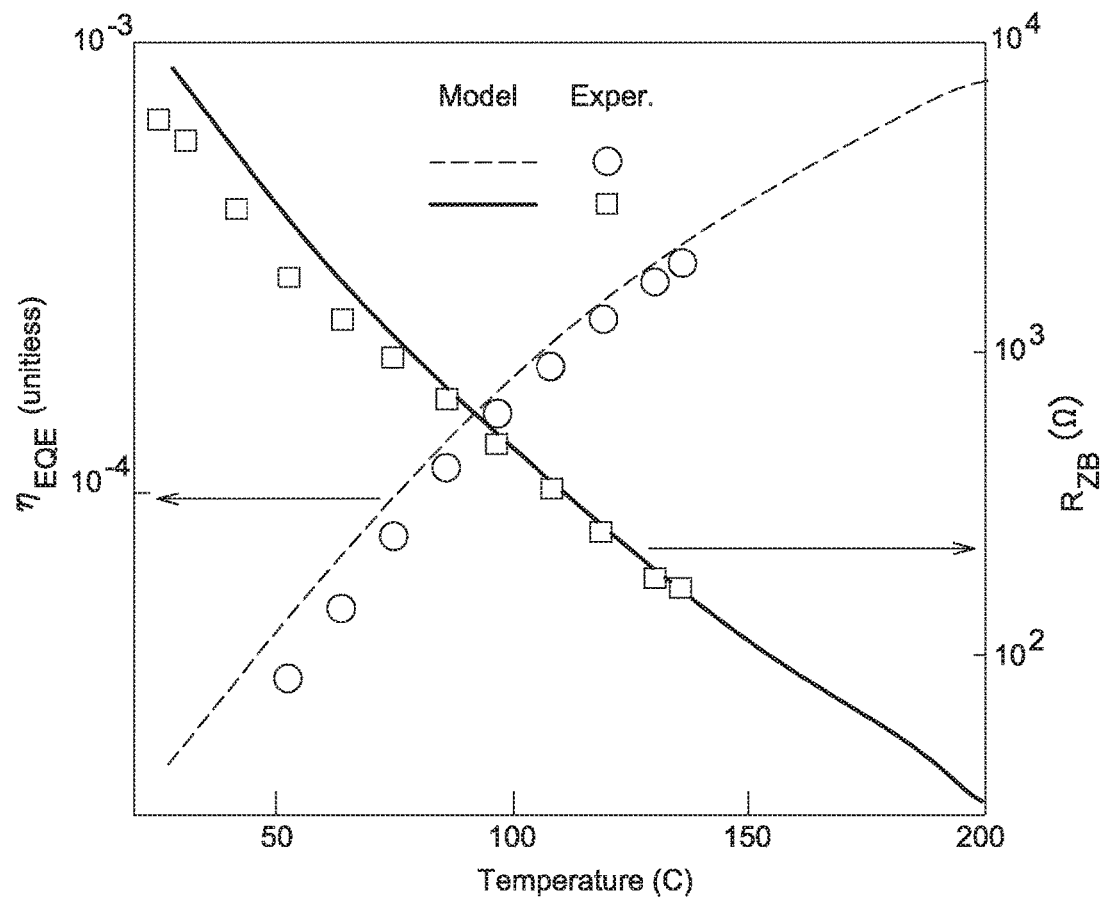
FIG. 13C is a plot of external quantum efficiency versus temperature for the LED of FIG. 12.

FIG. 13C is a plot of the external quantum efficiency $\eta_{EQE}$ (left axis) and zero-bias resistance $R_{ZB}$ (right axis) versus temperature. Again without being bound by any particular theory, the external quantum efficiency $\eta_{EQE}$ is often small at low bias because non-radiative SRH recombination associated with defect trap states dominates in the presence of defects in the semiconductor lattice. Trap states compete with equilibrium holes for the capture of excess electrons, and with equilibrium electrons for the capture of excess holes. Since the equilibrium carrier densities rise rapidly with temperature while the trap density does not, low-bias $\eta_{EQE}$ also rises with temperature, as shown in FIG. 13C. In this experiment a 24% increase in the absolute temperature resulted in a 10-fold rise in low-bias $\eta_{EQE}$.

Figure 14A:
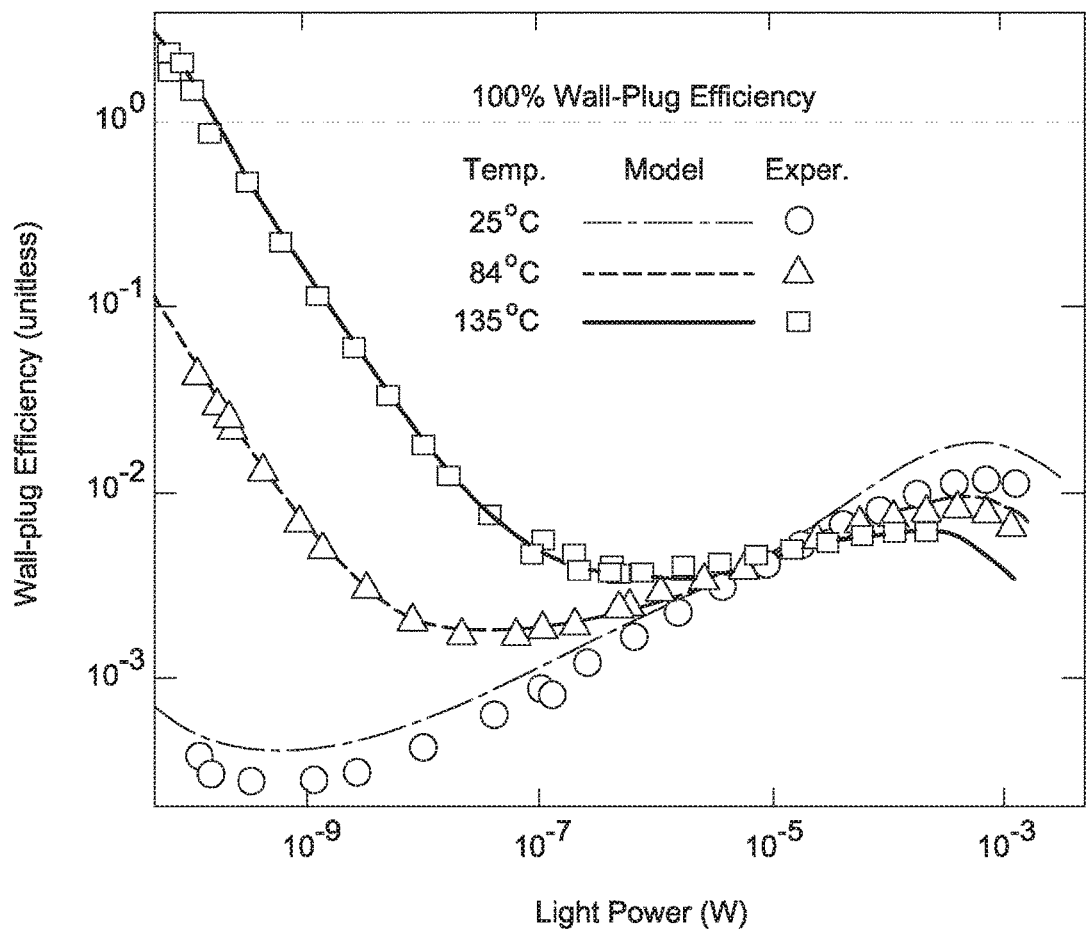
FIGS. 14A and 14B are plots of wall-plug efficiency versus optical power for the LED of FIG. 12 operating at different temperatures.
Figure 14B:
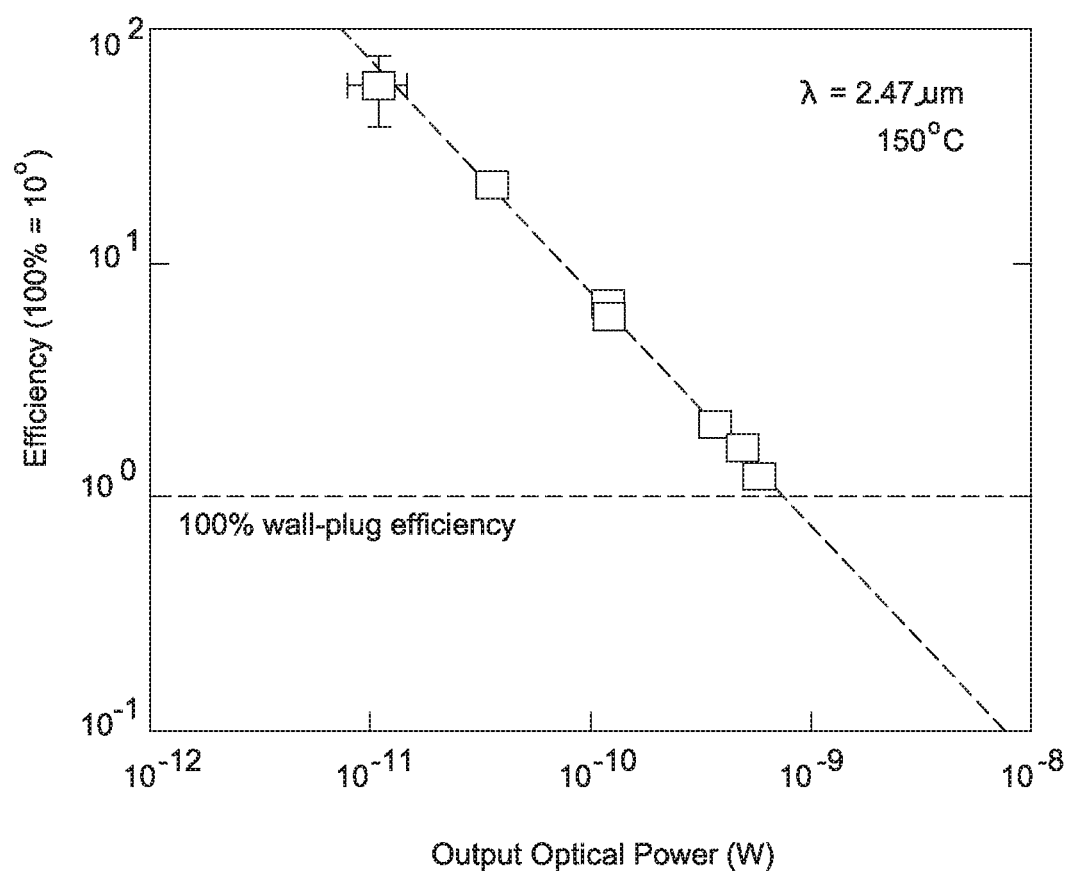

FIGS. 14A and 14B are plots of the LED's wall-plug efficiency versus optical output power at low bias for different operating temperatures and different ranges of output optical power. The dashed line in FIG. 14B indicates 100% wall-plug efficiency. FIGS. 14A and 14B show that the wall-plug efficiency varies inversely with optical output power at low bias. The external quantum efficiency $\eta_{EQE}$ is voltage-independent and the I-V characteristic is linear through the origin, as in the low-bias regime. FIGS. 14A and 14B also show that this behavior continues beyond the point of unity wall-plug efficiency, indicating net electro-luminescent cooling. Unlike strategies for cooling which work only above some minimum junction voltage, operating at low-bias may permit unbounded wall-plug efficiency at infinitesimal power. The existence of such a low-bias regime is a general, material-independent physical property of LEDs, which suggests that existing LEDs could be operated at low bias and thermally pumped to increase wall-plug efficiency.

Figure 15A:
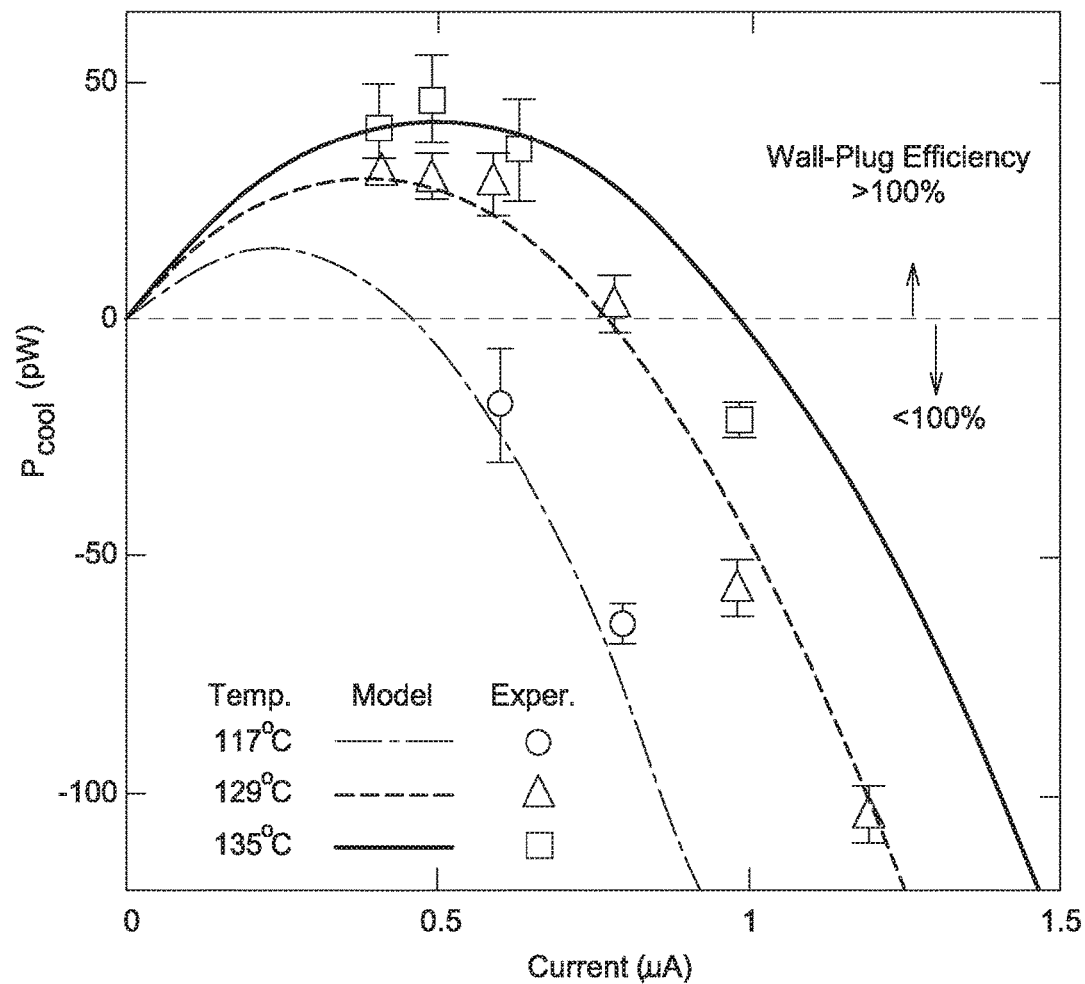
FIGS. 15A and 15B are plots of cooling power versus current for the LED of FIG. 12 operating at different temperatures.
Figure 15B:
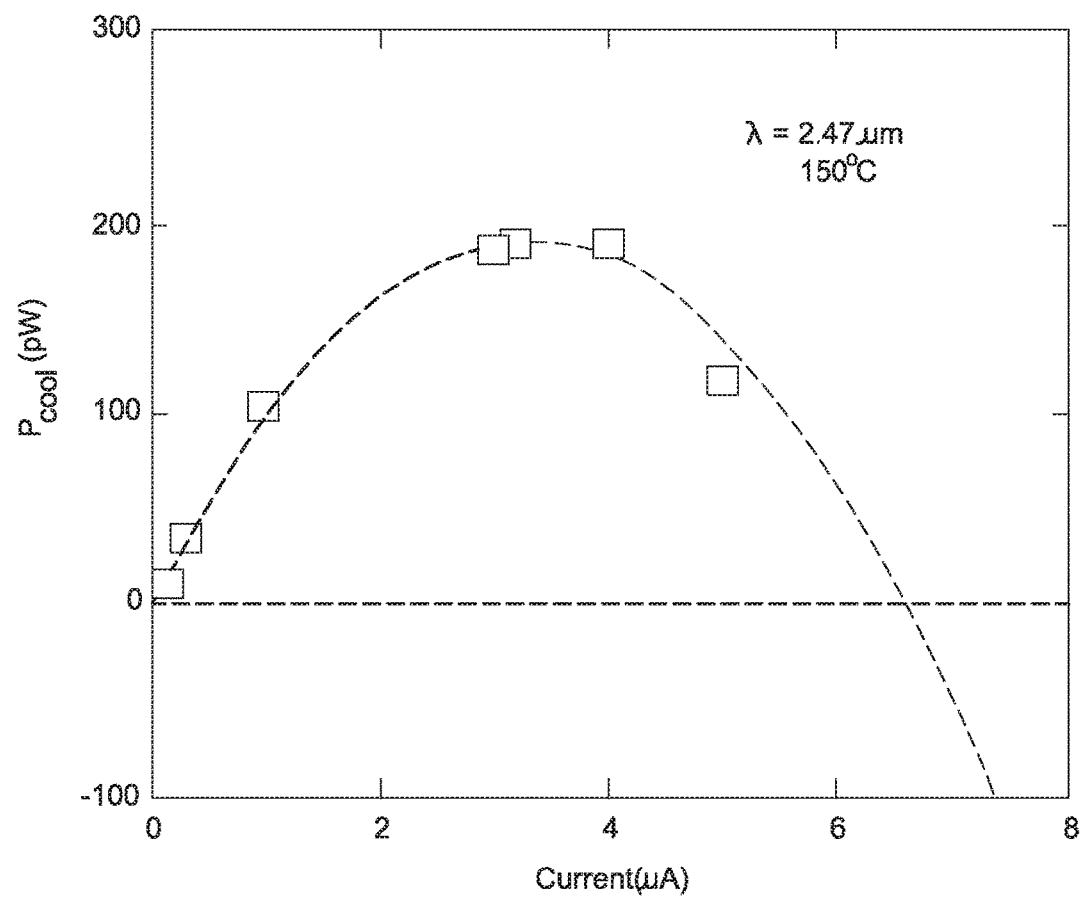

FIGS. 15A and 15B are plots of the LED's net cooling power $P_{cool}$ versus current for different temperatures. The dashed horizontal lines represent 100% wall-plug efficiency. Although the Peltier heat exchange of the injection process is highly non-uniform, on average the device remained very slightly cooled so that in steady-state the thermal energy that pumped the emitter flowed in from the ambient environment. The net cooling power, $P_{cool}$, is given by the difference between the emitted optical power and the input electrical power. In terms of the zero-bias resistance R and the current through the device I, the net cooling power is given by:

$$P_{cool} = I\left(\frac{\hbar\omega}{q} \cdot n_{EQE}\right) - I^2 R. \quad (17)$$

The bias resistance R is not indicative of a purely irreversible process as in an Ohmic resistance. Rather, at low bias, voltage and current are directly proportional and R, measured in Ohms, represents their ratio.

Without being bound by any particular theory, Equation (17) indicates that net cooling results from competition between a cooling process linear in current and a heating process quadratic in current. Here, low-bias LED operation is analogous to a thermo-electric cooler (as described above), in which Peltier heat transfer competes with Joule heating to realize heat pumping. In both devices a finite current maximizes cooling power and at lower currents there is a trade-off between power and efficiency. Moreover, as sources of irreversibility are removed from the LED, the LED acts as a reversible Carnot-efficient heat pump operating between the lattice and the photon field.

FIGS. 14-15 also show that both the maximum output power at unity efficiency and the maximum cooling power increase with temperature. When a small voltage is applied, the energy barrier to thermally assisted injection is lowered so that the product np rises as in the Shockley diode equation:

$$np = n_0 p_0 \cdot e^{qV/k_B T} \quad (18).$$

Hence for a given magnitude of the dimensionless excitation $qV/k_B T$, net recombination is proportional to the product of equilibrium electron and hole concentrations $n_0 p_0$. For non-degenerate regions, this reduces to the intrinsic carrier concentration squared. Since this quantity is a measure of the ambient environment's ability to thermally excite electrons across the bandgap, it is exponentially dependent on the ratio $E_{gap}/k_B T$:

$$n_0 p_0 \propto e^{-E_{gap}/k_B T} \quad (19).$$

Without being bound to any particular theory, this result explains the variation in low-bias behavior with temperature. Equation (19) also suggests that switching from 135° C. InGaAsSb (where $E_{gap}/k_B T \approx 15$) to these wider bandgap materials at 25° C. (where $E_{gap}/k_B T > 50$) would result in a reduction of the optical power available at low bias by roughly 15 orders of magnitude.

The experimental results in FIGS. 13-15 show that application of a forward bias voltage V less than the thermal voltage $k_B T/q$ imposes a small deviation from thermodynamic equilibrium on the device. In response, the rates of both radiative and non-radiative recombination have contributions at linear order in V and their ratio, the external quantum efficiency $\eta_{EQE}$, is voltage-independent. As a result, the LED's optical output power scales linearly with voltage while the input power scales quadratically, resulting in arbitrarily efficient photon generation accompanied by net electro-luminescent cooling of the solid at low bias.

As mentioned above, the extremely efficient electro-luminescence available at sub-thermal voltages could enable efficient high-temperature sources for lock-in spectroscopy. For instance, the LED shown in FIG. 12 could serve as an efficient source around 4130 cm$^{-1}$ in a 135° C. environment. As the wavelength is extended toward longer wavelengths, the associated decrease in $E_{gap}/k_B T$ may improve LED output power and widen the temperature range over which high efficiency is attained. In still higher-temperature environments, low-bias operation of infrared LEDs may be much more efficient and diminish the need for any active cooling. In fact, exposing an LED to exhaust gases from combustion and down-hole spectroscopy could elevate the LED's temperature, thereby increasing the LED's wall-plug efficiency.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A light-emitting diode (LED) comprising:
   an active region comprising at least one semiconductor configured to emit visible light via recombination of electrons and holes, the active region having a first side and a second side opposite the first side;
   a first electrode disposed on the first side of the active region, the first electrode comprising a reflective surface to reflect the visible light emitted by the at least one semiconductor;
   a second electrode disposed on the second side of the active region, the second electrode being substantially transparent to the visible light emitted by the at least one semiconductor; and
   a thermally insulating substrate, disposed on the first electrode and in thermal communication with the active region, to trap a substantial amount of heat generated by the active region so as to thermally assist injection of at least some of the electrons and holes into the active region,
   wherein the active region is configured to emit visible light at a wall plug efficiency of at least about 80% via recombination of at least some of the electrons and holes.

2. The LED of claim 1, wherein the active region comprises at least one of GaSb and InP.

3. The LED of claim 1, wherein the active region has a textured emitting surface on the second side to diffuse and/or scatter the visible light emitted by the at least one semiconductor.

4. The LED of claim 1, wherein the active region is not mounted on a heat sink.

5. The LED of claim 1, wherein the first electrode and the second electrode are configured to apply a forward bias of less than about 3.25 V to the active region during emission of the visible light.

6. The LED of claim 1, wherein the first electrode and the second electrode are configured to apply a forward bias voltage V to the active region, wherein $qV < \hbar\omega$, q is the charge of an electron, and $\hbar\omega$ is the energy of a photon emitted by the LED.

7. The LED of claim 1, wherein the second electrode comprises indium tin oxide.

8. The LED of claim 1, wherein the thermally insulating substrate comprises at least one of an oxide-based substrate and a polymer-based substrate.

9. The LED of claim 1, further comprising:
a micro-structure, in thermal communication with the active region, to increase heat transfer to the active region.

10. The LED of claim 1, further comprising:
a transparent encapsulant, substantially enclosing the second side of the active region, to protect an emitting surface of the active region on the second side.

11. A method of operating a light-emitting diode (LED), the method comprising:
applying a forward bias voltage to an active region using a first electrode disposed on a first side of the active region and a second electrode disposed on a second side, opposite the first side, of the active region, thereby causing the active region to emit visible light via recombination of electrons and holes, the first electrode comprising a reflective surface to reflect the visible light emitted by the at least one semiconductor, the second electrode being substantially transparent to the visible light emitted by the at least one semiconductor; and
trapping a substantial amount of heat generated by the active region, using a thermally insulating substrate, disposed on the first electrode and in thermal communication with the active region, so as to thermally assist injection of the electrons and holes into the active region,
wherein trapping the substantial amount of the heat comprises increasing a wall plug efficiency of the LED to at least about 80% via recombination of at least some of the electrons and holes.

12. The method of claim 11, wherein applying the forward bias voltage comprises applying a voltage V to the active region, wherein $qV < h\omega$, q is the charge of an electron, and $h\omega$ is the photon energy of a photon emitted by the LED.

13. The method of claim 11, wherein applying the forward bias voltage comprises applying less than about 3.25 V to the active region.

14. The method of claim 11, wherein trapping the substantial amount of the heat comprises heating the active region of the LED to a temperature of at least about 400 K.

15. The method of claim 11, wherein the active region is configured to emit light from at least one semiconductor having an external quantum efficiency of equal to or greater than about 75%.

16. The method of claim 11, further comprising:
diffusing and/or scattering the visible light emitted by the active region via a textured emitting surface on the second side of the active region.

17. The method of claim 11, further comprising:
increasing heat transfer to the active region using a micro-structure in thermal communication with the active region.

18. A light-emitting diode (LED) comprising:
an active region comprising at least one of GaSb and InP and configured to emit visible light at a wall plug efficiency of at least about 80% via recombination of electrons and holes, the active region having a first side and a second side opposite the first side, the active region having a textured emitting surface on the second side to diffuse and/or scatter the visible light;
a first electrode disposed on the first side of the active region, the first electrode comprising a reflective surface to reflect the visible light emitted by the at least one semiconductor;
a second electrode disposed on the second side of the active region, the second electrode being substantially transparent to the visible light emitted by the active region; and
a thermally insulating substrate comprising at least one of an oxide-based substrate and a polymer-based substrate, disposed on the first electrode and in thermal communication with the active region, to trap a substantial amount of heat generated by the active region so as to thermally assist injection of the electrons and holes into the active region.

* * * * *